US009956285B2

(12) United States Patent
Iadonato et al.

(10) Patent No.: US 9,956,285 B2
(45) Date of Patent: May 1, 2018

(54) ANTI-VIRAL COMPOUNDS

(71) Applicant: Kineta, Inc., Seattle, WA (US)

(72) Inventors: Shawn P. Iadonato, Seattle, WA (US);
Kristin M. Bedard, Bellevue, WA (US); Myra Wang Imanaka, Seattle, WA (US); Kerry W. Fowler, Seattle, WA (US)

(73) Assignee: Kineta, Inc., Seattle, WA (US)

( * ) Notice: Subject to any disclaimer, the term of this patent is extended or adjusted under 35 U.S.C. 154(b) by 0 days. days.

(21) Appl. No.: 15/419,784

(22) Filed: Jan. 30, 2017

(65) Prior Publication Data

US 2017/0258897 A1 Sep. 14, 2017

Related U.S. Application Data

(63) Continuation of application No. 14/348,516, filed as application No. PCT/US2012/057646 on Sep. 27, 2012, now Pat. No. 9,555,106.

(60) Provisional application No. 61/542,049, filed on Sep. 30, 2011.

(51) Int. Cl.
*A61K 31/429* (2006.01)
*A61K 39/39* (2006.01)
*A61K 39/00* (2006.01)

(52) U.S. Cl.
CPC ............ *A61K 39/39* (2013.01); *A61K 31/429* (2013.01); *A61K 39/00* (2013.01); *A61K 2039/55511* (2013.01); *A61K 2039/57* (2013.01); *A61K 2039/575* (2013.01)

(58) Field of Classification Search
CPC .................................................. A61K 31/429
See application file for complete search history.

(56) References Cited

U.S. PATENT DOCUMENTS 3,489,558 A  1/1970 Clecak et al.
2010/0267717 A1 10/2010 Leban et al.

FOREIGN PATENT DOCUMENTS

WO 01/57008 A1 8/2001
WO 2004/078115 A2 9/2004
WO 2010/008847 A2 1/2010
WO 2010/024903 A1 3/2010
WO 2011/002635 A1 1/2011
WO 2013/049407 A2 4/2013

OTHER PUBLICATIONS

Schickli et al., Human Vaccines, vol. 5, Issue 9, pp. 582-591, Sep. 2009.*
Chemical Abstracts Registry No. 681228-48-8, indexed in the Registry file on STN CAS Online, May 12, 2004.
Examination Report dated Feb. 9, 2016, issued in corresponding ARIPO Application No. AP/P/2014/007595, filed Sep. 27, 2012, 5 pages.
Further Examination Report dated May 13, 2016, issued in corresponding New Zealand Application No. 622636, filed Mar. 18, 2014, 3 pages.
International Preliminary Report on Patentability dated Jul. 30, 2015, in International Application No. PCT/US2014/011714, 10 pages.
Office Action dated Oct. 7, 2015 in Israel Application No. 231780, 4 pages.
Office Action dated Jul. 16, 2014 in Israel Application No. 231780.
Office Action dated Feb. 6, 2014 in U.S. Appl. No. 13/765,583, filed Feb. 12, 2013.
Pesin, V.G., and I.G. Vitenberg, "Salts of Dialkyl and Diaryl Hydrogen Phosphoro—Thioates and -Dithioates VII. Reactions of Salts of O,O-Diethyl Hydrogen Phosphoro—Thioate and -Dithioate With Aromatic and Heterocyclic Halogen Derivatives," Journal of General Chemistry of the USSR 26(7):1283-1289, Jul. 1966
PubChem CID 9879593—National Center for Biotechnology Information. PubChem Compound Database; CID=9879593, https://pubchem.ncbi.nlm.nih.gov/compound/9879593 (accessed Jun. 14, 2016), create date Oct. 25, 2006.
PubChemCompound, datasheet [online compound summary], National Center for Biotechnology Information. PubChem Compound Database; CID=4149223, <https://pubchem.ncbi.nlm.nih.gov/compound/4149223>, 14 pages, Sep. 13, 2005.
Search Report & Written Opinion dated Apr. 20, 2015, in Singapore Application No. 11201401084T.
Written Opinion dated Feb. 26, 2016, issued in corresponding Singapore Application No. 11201401084T, filed Sep. 27, 2012, 5 pages.
Bhavsar, D., et al., "Synthesis and In Vitro Anti-HIV Activity of N-1,3-benzo[d]thiazol-2-yl-2-(2-oxo-2H-chromen-4-yl) acetamide Derivatives Using MTT Method," Bioorganic & Medicinal Chemistry Letters 21(11):3443-3446, Jun. 2011.
Chakrabarty, M., et al., "An Expedient Synthesis of Novel 2-Substituted Thiazolo[4,5-f]isoquinolines/quinolines and Benzo[1,2-d:4,3-d']bisthiazoles and Their Potential as Inhibitors of COX-1 and COX-2," Archive for Organic Chemistry (ARKIVOC) 2010(11):265-290, Nov. 2010.
Chemical Abstracts Registry No. 313262-11-2, indexed in the Registry file on STN CAS Online Jan. 9, 2001 [retrieved Mar. 15, 2016], 1 page.
Chemical Abstracts Registry No. 325978-29-8, indexed in the Registry file on STN CAS Online Mar. 7, 2001 [retrieved Mar. 15, 2016], 1 page.
Chemical Abstracts Registry No. 325978-43-6, indexed in the Registry file on STN CAS Online Mar. 7, 2001 [retrieved Mar. 15, 2016], 1 page.
Chemical Abstracts Registry No. 361482-14-6, indexed in the Registry file on STN CAS Online Oct. 11, 2001 [retrieved Mar. 15, 2016], 1 page.

(Continued)

*Primary Examiner* — Laura L. Stockton
(74) *Attorney, Agent, or Firm* — Christensen O'Connor Johnson Kindness PLLC

(57) ABSTRACT

Disclosed herein are compounds and related compositions for the treatment of viral infection, including RNA viral infection, and compounds that can modulate the RIG-I pathway in vertebrate cells, including compounds that can activate the RIG-I pathway.

6 Claims, 14 Drawing Sheets

(56) References Cited

OTHER PUBLICATIONS

Chemical Abstracts Registry No. 476631-72-8, indexed in the Registry file on STN CAS Online Dec. 18, 2002 [retrieved Mar. 15, 2016], 1 page.
PubChem Compound Database, National Center for Biotechnology Information, CID=3529501, <https://pubchem.ncbi.nlm.nih.gov/compound/3529501> [accessed Mar. 15, 2016], create date Sep. 8, 2005, 12 pages.
PubChem Compound Database, National Center for Biotechnology Information, CID=3626425, <https://pubchem.ncbi.nlm.nih.gov/compound/3626425> [accessed Mar. 16, 2016], create date Sep. 9, 2016, 12 pages.
PubChem Compound Database, National Center for Biotechnology Information, CID=4461530, <https://pubchem.ncbi.nlm.nih.gov/compound/4461530> [accessed Mar. 16, 2016], create date Sep. 15, 2005, 10 pages.
PubChemCompound, datasheet [online compound summary], National Center for Biotechnology Information, PubChem Compound Database; CID=4646016 <http://pubchem.ncbi.nlm.nih.gov/search/search.cgi>, create date Sep. 16, 2005, 3 pages.
PubChemCompound, datasheet [online compound summary], National Center for Biotechnology Information, PubChem Compound Database; CID=3244649 <http://pubchem.ncbi.nlm.nih.gov/search/search.cgi>, create date Aug. 16, 2005, 3 pages.
PubChemCompound, datasheet [online compound summary], National Center for Biotechnology Information, PubChem Compound Database; CID=4137760 <http://pubchem.ncbi.nlm.nih.gov/search/search.cgi>, create date Sep. 13, 2005, 4 pages.
Search Report and Written Opinion, dated Mar. 27, 2013, for PCT/US2012/057646, filed Sep. 27, 2012, 5 pages.

\* cited by examiner

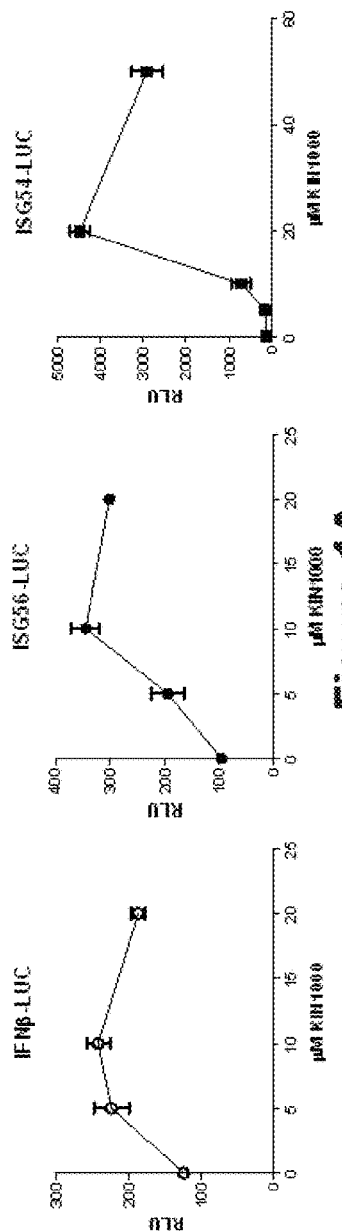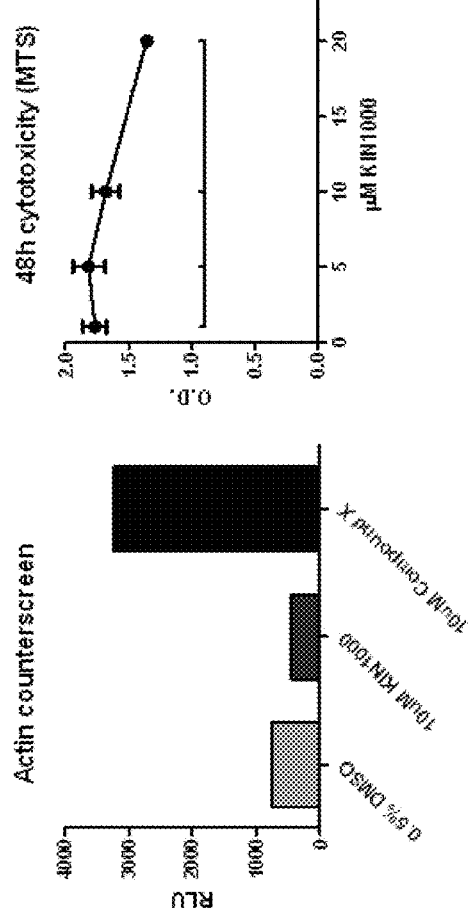

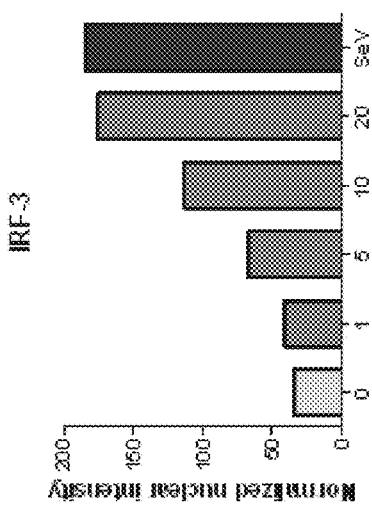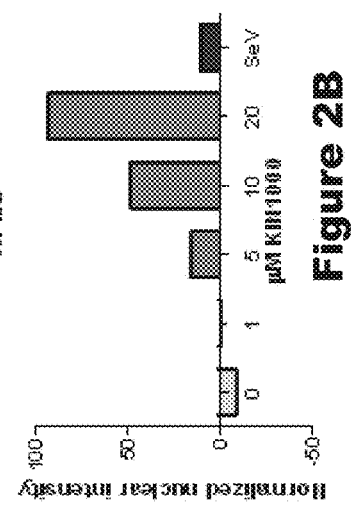

ANTI-VIRAL COMPOUNDS

CROSS-REFERENCES TO RELATED APPLICATIONS

This application is a continuation of U.S. patent application Ser. No. 14/348,516, filed Mar. 28, 2014, which is the national stage of International Application No. PCT/US2012/057646, filed Sep. 27, 2012, which claims the benefit of U.S. Provisional Application No. 61/542,049, filed Sep. 30, 2011. Each application is incorporated herein by reference in its entirety.

FIELD OF THE DISCLOSURE

Compounds and methods disclosed herein are useful for treating viral infection in vertebrates, including RNA viral infections.

BACKGROUND OF THE DISCLOSURE

As a group, RNA viruses represent an enormous public health problem in the U.S. and worldwide. Well-known RNA viruses include influenza virus (including the avian and swine isolates), hepatitis C virus (HCV), West Nile virus, SARS-coronavirus, respiratory syncytial virus (RSV), and human immunodeficiency virus (HIV).

More than 170 million people worldwide are infected by HCV, and 130 million of those are chronic carriers at risk of developing chronic liver diseases (cirrhosis, carcinoma, and liver failure). As such, HCV is responsible for two thirds of all liver transplants in the developed world. Recent studies show that the death rate from HCV infection is rising due to the increasing age of chronically infected patients. Likewise seasonal flu infects 5-20% of the population resulting in 200,000 hospitalizations and 36,000 deaths each year.

Compared to influenza and HCV, West Nile virus causes the lowest number of infections, 981 in the United States in 2010. Twenty percent of infected patients develop a severe form of the disease, resulting in a 4.5% mortality rate. Unlike influenza and HCV, there are no approved therapies for the treatment of West Nile virus infection, and it is a high-priority pathogen for drug development due to its potential as a bioterrorist agent.

Among the RNA viruses listed, vaccines exist only for influenza virus. Accordingly, drug therapy is essential to mitigate the significant morbidity and mortality associated with these viruses. Unfortunately, the number of antiviral drugs is limited, many are poorly effective, and nearly all are plagued by the rapid evolution of viral resistance and a limited spectrum of action. Moreover, treatments for acute influenza and HCV infections are only moderately effective. The standard of care for HCV infection, PEGylated interferon and ribavirin, is effective in only 50% of patients, and there are a number of dose-limiting side effects associated with the combined therapy. Both classes of acute influenza antivirals, adamantanes and neuraminidase inhibitors, are only effective within the first 48 hours after infection, thereby limiting the window of opportunity for treatment. High resistance to adamantanes already restricts their use, and massive stockpiling of neuraminidase inhibitors will eventually lead to overuse and the emergence of resistant strains of influenza.

Most drug development efforts against these viruses target viral proteins. This is a large part of the reason that current drugs are narrow in spectrum and subject to the emergence of viral resistance. Most RNA viruses have small genomes and many encode less than a dozen proteins. Viral targets are therefore limited. Based on the foregoing, there is an immense and unmet need for effective treatments against viral infections.

SUMMARY OF THE DISCLOSURE

The compounds and methods disclosed herein shift the focus of viral drug development away from the targeting of viral proteins to the development of drugs that target and enhance the host's innate antiviral response. Such compounds and methods are likely to be more effective, less susceptible to the emergence of viral resistance, cause fewer side effects and be effective against a range of different viruses.

The RIG-I pathway 08520 is intimately involved in regulating the innate immune response to RNA virus infections. RIG-I agonists are expected to be useful for the treatment of many viruses including, without limitation, HCV, influenza, and West Nile virus. Accordingly, the present disclosure relates to compounds and methods for treating viral infection, including infection by RNA viruses, wherein the compounds can modulate the RIG-I pathway.

One embodiment of the present disclosure includes a compound represented by the formula

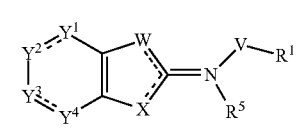

Formula 1 wherein a dashed line indicates the presence or absence of a bond; $R^1$ may be $R^a$, $OR^2$ or $NR^2R^3$; each $R^a$ may independently be independently H, optionally substituted hydrocarbyl, optionally substituted aryl, optionally substituted heteroaryl; $R^2$ and $R^3$ may each independently be $R^a$, $COR^a$, or $SO_2R^a$; $Y^1$, $Y^2$, $Y^3$ and $Y^4$ may each independently be $CR^4$ or N; each $R^4$ may independently be $R^2$, $OR^a$, $NR^2R^3$, $SR^a$, $SOR^a$, $SO_2R^a$, $SO_2NHR^a$, $NCOR^a$, halogen, trihalomethyl, CN, S=O, or nitro; $R^5$ may be $R^a$, $COR^a$, $SO_2R^a$, or is not present; V may be $CR^2$, $CR^2R^3$, C=O, $COCR^2R^3$, or $C=NR^2$; and, W and X may each independently be N, $NR^a$, O, S, $CR^2R^4$ or $CR^4$.

Some embodiments of the present disclosure include a compound represented by the formula (the "KIN1000" compound):

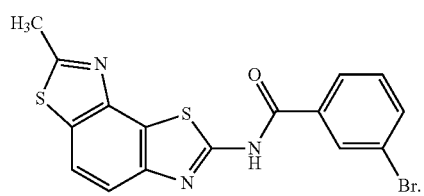 [SMILES: Cc1nc2c(ccc3nc(NC(=O)c4cccc(Br)c4)sc32)s1]

Additional embodiments include a compound represented by the formula

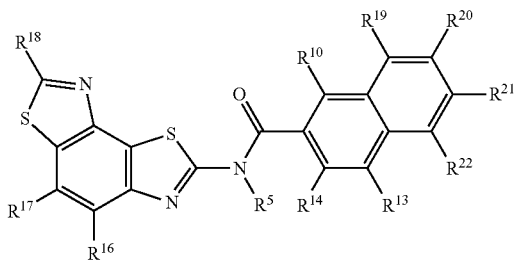

wherein $R^{10}$, $R^{13}$, $R^{14}$, $R^{16}$, $R^{17}$, $R^{18}$, $R^{19}$, $R^{20}$, $R^{21}$, and $R^{22}$ are independently $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, Cl, Br, I, or $C_{2-5}$ heterocyclyl; each $R^b$ is independently H or $C_{1-3}$ hydrocarbyl, and each $R^c$ is independently H or $C_{1-3}$ alkyl.

Further embodiments of the present disclosure include a compound represented by the formula (the "KIN1148" compound):

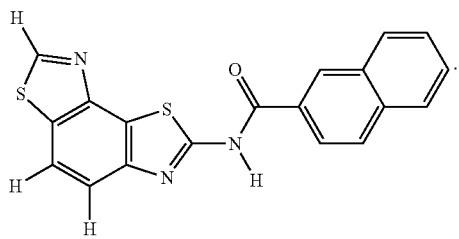 [SMILES: O=C(Nc1nc2ccc3scnc3c2s1)c1ccc2ccccc2c1]

Some embodiments of the present disclosure include a pharmaceutical composition comprising any of the compounds as described herein.

Some embodiments of the present disclosure include methods of treating or preventing a viral infection in a vertebrate comprising administering to the vertebrate a pharmaceutical composition as described herein. In some embodiments, the viral infection is caused by a virus from one or more of the following families: Arenaviridae, Astroviridae, Birnaviridae, Bromoviridae, Bunyaviridae, Caliciviridae, Closteroviridae, Comoviridae, Cystoviridae, Flaviviridae, Flexiviridae, Hepevirus, Leviviridae, Luteoviridae, Mononegavirales, Mosaic Viruses, Nidovirales, Nodaviridae, Orthomyxoviridae, Picobirnavirus, Picornaviridae, Potyviridae, Reoviridae, Retroviridae, Sequiviridae, Tenuivirus, Togaviridae, Tombusviridae, Totiviridae, Tymoviridae, Hepadnaviridae, Herpesviridae, Paramyxoviridae or Papillomaviridae. In some embodiments, the viral infection is influenza virus, Hepatitis C virus, West Nile virus, SARS-coronavirus, poliovirus, measles virus, Dengue virus, yellow fever virus, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, Kyasanur forest disease virus, respiratory syncytial virus or HIV.

Some embodiments of the methods of the present disclosure include administering any of the pharmaceutical compositions described herein as an adjuvant for a prophylactic or therapeutic vaccine. In some embodiments, the method includes vaccinating a vertebrate by additionally administering a vaccine against influenza virus, Hepatitis C virus, West Nile virus, SARS-coronavirus, poliovirus, measles virus, Dengue virus, yellow fever virus, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, Kyasanur forest disease virus or HIV.

Some embodiments of the present disclosure include methods of modulating the innate immune response in a eukaryotic cell, comprising administering to the cell any of the compounds as described herein. In some embodiments the cell is in vivo. In other embodiments the cell is in vitro.

BRIEF DESCRIPTION OF THE DRAWINGS

FIGS. 1A-1C show validation and characterization of compound KIN1000 ("RLU"=relative luciferase units). In FIG. 1A, initial "hit" compounds were validated by demonstrating dose-dependent induction of the IFNβ-luciferase (IFNβ-LUC, left), ISG56-luciferase (ISG56-LUC, center), and the ISG54-luciferase (ISG54-LUC, right) reporter genes. FIG. 1B confirms the specificity of KIN1000, which does not induce the non-specific β-actin promoter ("0.5% DMSO"=vehicle control; "10 µM KIN1000"=β-actin-luciferase reporter in presence of KIN1000; "10 µM Compound X"=positive control β-actin induction). In FIG. 1C, the MTS assay demonstrated that KIN1000 did not show evident cytotoxicity to human cells treated for 48 hours with the compound. The O.D. value that represents 50% cell mortality is shown by a horizontal line, also demonstrating that the CC50 of KIN1000 is greater than 20 µM.

FIGS. 2A and 2B show activation of transcription factors by KIN1000. In FIG. 2A, HeLa cells treated with increasing amounts of KIN1000 showed dose-dependent increase in IRF-3 translocation to the nucleus, quantified by nuclear intensity minus cytoplasmic intensity ("normalized nuclear intensity"). In FIG. 2B, HeLa cells treated with increasing amounts of KIN1000 showed dose-dependent increase in NFκB translocation, quantified by nuclear intensity minus cytoplasmic intensity. "SeV" refers to Sendai virus infection, the positive control.

FIG. 5A shows gene expression levels of IFIT2 (left) and OAS1 (right) in HeLa cells over time from 4-24 hours post treatment with 10 uM KIN1000 (grey) or KIN1148 (black). FIG. 5B shows gene expression levels of IFIT2 in PH5CH8 cells (left) treated with KIN1000 (solid grey bars) or KIN1148 (solid black bars), and in HeLa cells (right) treated with KIN1000 (grey striped bars) or KIN1148 (black checked bars). In each test group, the three vertical bars represent 5, 10, and 20 µM compound (KIN1000 or KIN1148), respectively. FIG. 5C shows gene expression levels of IFIT2 (left), OAS1 (center), and MxA (right) in primary HUVEC cells that were treated with 1 µM KIN1000 (grey) or 1 µM KIN1148 (black).

FIG. 6A shows that HeLa cells treated with increasing amount of KIN1000 and KIN1148 showed dose-dependent decrease in infection by RSV. FIG. 6B shows that KIN1148 showed antiviral activity against RSV when drug is added up to 24 hours prior to infection.

DETAILED DESCRIPTION

Figure 3:
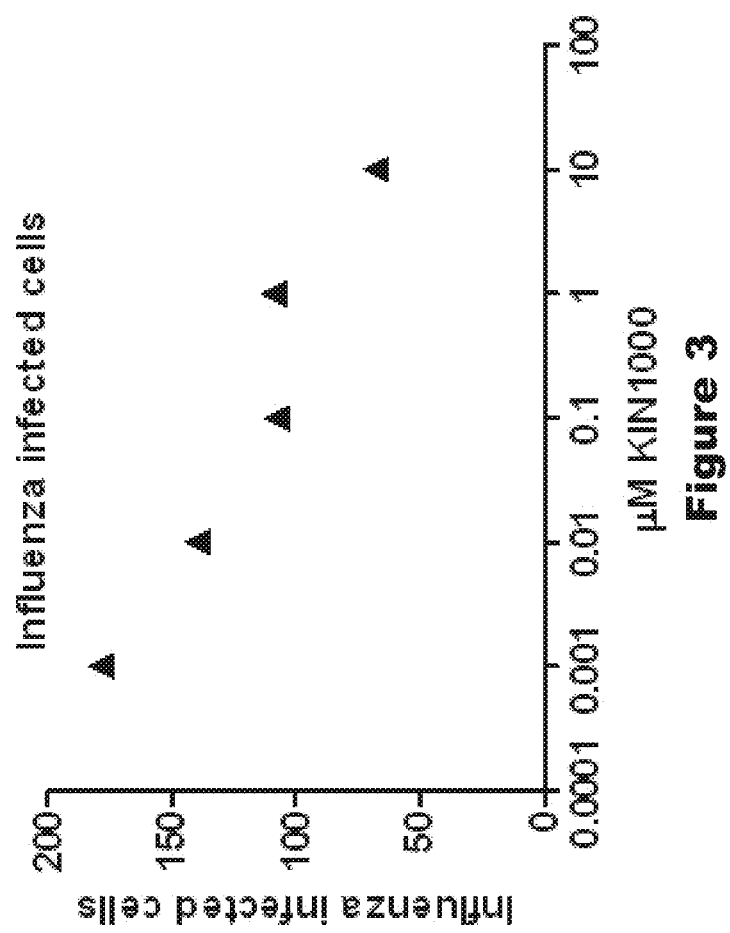
FIG. 3 shows anti-viral activity of KIN1000. MRCS cells treated with increasing amounts of KIN1000 showed dose-dependent decrease in infection by influenza virus.

The present disclosure provides compounds and methods that shift the focus of viral treatments away from the targeting of viral proteins to the development of drugs that target and enhance the host (patient's) innate antiviral response. Such compounds and methods are likely to be more effective, less susceptible to the emergence of viral resistance, cause fewer side effects and be effective against a range of different viruses.

The RIG-I pathway is intimately involved in regulating the innate immune response to RNA virus infections. RIG-I is a cytosolic pathogen recognition receptor that is essential for triggering immunity to a wide range of RNA viruses. RIG-I is a double-stranded RNA helicase that binds to motifs within the RNA virus genome characterized by homopolymeric stretches of uridine or polymeric U/A motifs. Binding to RNA induces a conformation change that relieves RIG-I signaling repression by an autologous repressor domain, thus allowing RIG-I to signal downstream through its tandem caspase activation and recruitment domains (CARDs). RIG-I signaling is dependent upon its NTPase activity, but does not require the helicase domain. RIG-I signaling is silent in resting cells, and the repressor domain serves as the on-off switch that governs signaling in response to virus infection.

RIG-I signaling is transduced through IPS-1 (also known as Cardif, MAVs, and VISA), an essential adaptor protein that resides in the outer mitochondrial membrane. IPS-1 recruits a macromolecular signaling complex that stimulates the downstream activation of IRF-3, a transcription factor that induces the expression of type I IFNs and virus-responsive genes that control infection. Compounds that trigger RIG-I signaling directly or through modulation of RIG-I pathway components, including IRF-3, present attractive therapeutic applications as antivirals or immune modulators.

A high-throughput screening approach was used to identify compounds that modulate the RIG-I pathway, a key regulator of the cellular innate immune response to RNA virus infection. In particular embodiments, validated RIG-I agonist lead compounds were demonstrated to specifically activate interferon regulatory factor-3 (IRF-3). In additional embodiments they exhibit one or more of the following: they induce the expression of interferon-stimulated genes (ISGs), have low cytotoxicity in cell-based assays, are suitable for analog development and SAR studies, have drug-like physiochemical properties, and have antiviral activity against influenza A virus and/or HCV.

As discussed below, these compounds represent a new class of potential antiviral therapeutics. Although the disclosure is not bound by a specific mechanism of action of the compounds in vivo, the compounds are selected for their modulation of the RIG-I pathway. In certain embodiments, the modulation is activation of the RIG-I pathway. Compounds and methods disclosed herein function to, one or more of, decrease viral protein, viral RNA, and infectious virus in cell culture models of HCV and/or influenza virus.

In one embodiment, the disclosure herein relates to a class of compounds of represented by the following formula:

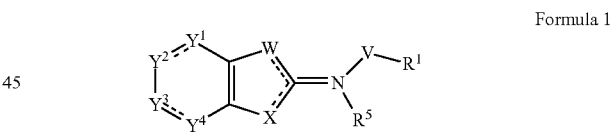

Formula 1 wherein a dashed line indicates the presence or absence of a bond; $R^1$ may be $R^a$, $OR^2$ or $NR^2R^3$; each $R^a$ may independently be independently H, optionally substituted hydrocarbyl, optionally substituted aryl, optionally substituted heteroaryl; $R^2$ and $R^3$ may each independently be $R^a$, $COR^a$, or $SO_2R^a$; $Y^1$, $Y^2$, $Y^3$ and $Y^4$ may each independently be $CR^4$ or N; each $R^4$ may independently be $R^2$, $OR^a$, $NR^2R^3$, $SR^a$, $SOR^a$, $SO_2R^a$, $SO_2NHR^a$, $NCOR^a$, halogen, trihalomethyl, CN, S=O, or nitro; $R^5$ may be $R^a$, $COR^a$, $SO_2R^a$, or is not present; V may be $CR^2$, $CR^2R^3$, C=O, $COCR^2R^3$, or $C=NR^2$; and, W and X may each independently be N, $NR^a$, O, S, $CR^2R^4$ or $CR^4$.

With respect to Formula 1, $Y^1$ may be $CR^4$ or N. In some embodiments, $Y^1$ is $CR^4$.

With respect to Formula 1, $Y^2$ may be $CR^4$ or N. In some embodiments, $Y^2$ is $CR^4$.

In some embodiments, $Y^1$ and $Y^2$ are both $CR^4$, and together form an additional heterocyclic ring optionally substituted by $R^{18}$. In some embodiments, V may be:

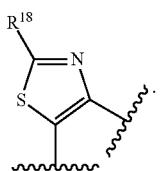

With respect to Formula 1, $Y^3$ may be $CR^4$ or N. In some embodiments, $Y^3$ is $CR^4$.

With respect to Formula 1, $Y^4$ may be $CR^4$ or N. In some embodiments, $Y^4$ is $CR^4$.

In some embodiments, $Y^1$, $Y^2$, $Y^3$ and $Y^4$ are $CR^4$. In some embodiments, $Y^1$, $Y^2$, $Y^3$ and $Y^4$ are CH. In some embodiments, $Y^1$ and $Y^2$ are

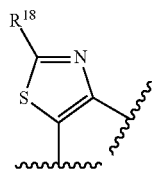

and $Y^3$ and $Y^4$ are CH.

Some embodiments include compounds represented by any of Formulas 2-12.

Formula 2

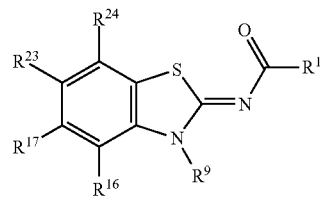

Formula 3

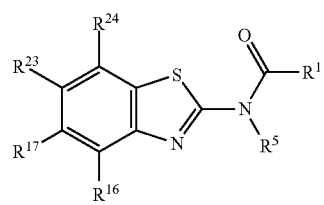

Formula 4

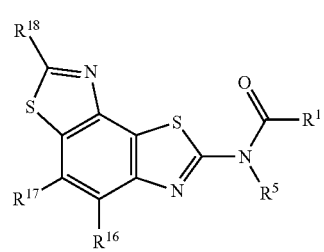

Formula 5

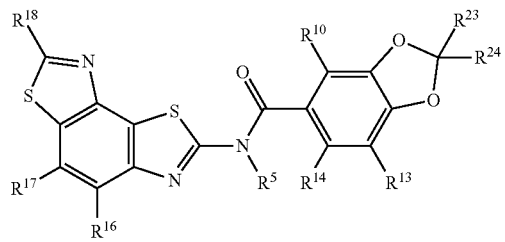

Formula 6

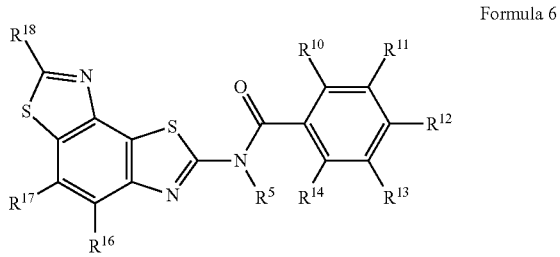

Formula 7

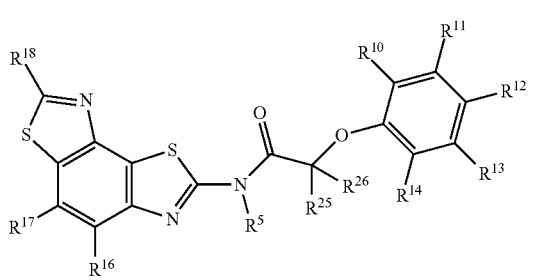

Formula 8

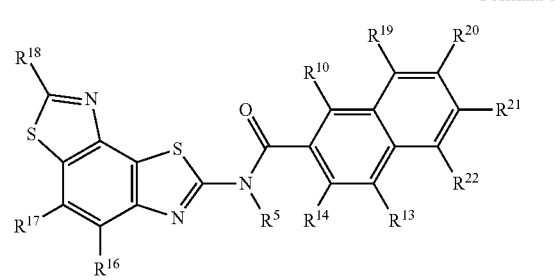

Formula 9

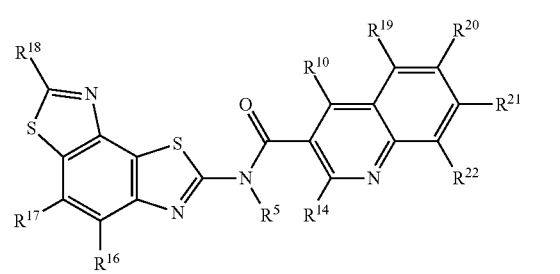

Formula 10

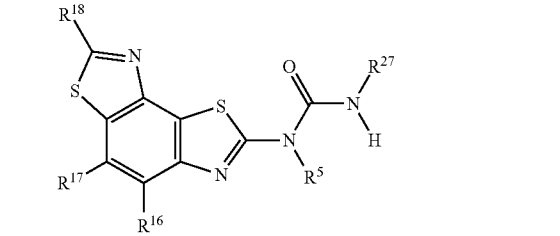

-continued

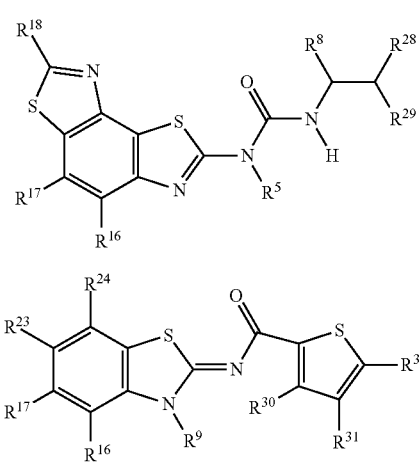

Formula 11

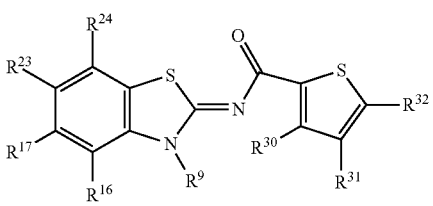

Formula 12

With respect to any relevant structural feature herein, each $R^a$ can independently be H; optionally substituted hydrocarbyl, such as $C_{1-12}$ or $C_{1-6}$ hydrocarbyl; optionally substituted aryl, such as optionally substituted $C_{6-12}$ aryl, including optionally substituted phenyl; optionally substituted heteroaryl, including optionally substituted $C_{2-12}$ heteroaryl, such as optionally substituted pyridinyl, optionally substituted furyl, optionally substituted thienyl, etc. In some embodiments, each $R^a$ can independently be H, or $C_{1-12}$ alkyl, including: linear or branched alkyl having the formula $C_aH_{a+1}$, or cycloalkyl having the formula $C_aH_{a-1}$, wherein a is 1, 2, 3, 4, 5, 6, 7, 8, 9, 10, 11, or 12, such as linear or branched alkyl of the formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of the formula: $C_3H_5$, $C_4H_7$, $C_5H_9$, $C_6H_{11}$, $C_7H_{13}$, $C_8H_{15}$, $C_9H_{17}$, $C_{10}H_{19}$, etc.

With respect to $R^a$, in some embodiments, the aryl group is substituted with halogen, trihalomethyl, alkoxy, alkylamino, OH, CN, alkylthio, arylthio, sulfoxide, arylsulfonyl, alkylsulfonyl, carboxylic acid, nitro or acylamino.

With respect to $R^a$, in some embodiments, the heteroaryl group is single or fused. In some embodiments, the single heteroaryl group is imidazole. In some embodiments, the fused heteroaryl group is benzimidazole. In some embodiments, the heteroaryl group is substituted with halogen, trihalomethyl, alkoxy, alkylamino, OH, CN, alkylthio, arylthio, sulfoxide, arylsulfonyl, alkylsulfonyl, carboxylic acid, nitro or acylamino. In some embodiments, the alkyl group is branched, cyclic or polycyclic.

With respect to $R^a$, a hydrocarbyl may be alkyl, alkenyl, or alkynyl. In some embodiments, the alkyl group is substituted with halogen, trihalomethyl, alkoxy, alkylamino, OH, CN, heteroaryl, alkylthio, arylthio, sulfoxide, arylsulfonyl, alkylsulfonyl, carboxylic acid, nitro, or acylamino. In some embodiments, the heteroaryl group is single or fused. In some embodiments, the single heteroaryl group is imidazole. In some embodiments, the fused heteroaryl group is benzimidazole. In some embodiments, the alkenyl group is branched, cyclic or polycyclic. In some embodiments, the alkenyl group is substituted with halogen, trihalomethyl, alkoxy, alkylamino, OH, CN, heteroaryl, alkylthio, arylthio, sulfoxide, arylsulfonyl, alkylsulfonyl, carboxylic acid, nitro, or acylamino.

With respect to any relevant structural feature herein, $R^b$ may be H, or $C_{1-3}$ hydrocarbyl, such as $CH_3$, $C_2H_5$, $C_3H_7$, cyclopropyl, $CH=CH_2$, $CH_2CH=CH_2$, $C\equiv CH$, $CH_2C\equiv CH$, etc.

With respect to any relevant structural feature herein, $R^c$ may be H, or $C_{1-3}$ alkyl, such as $CH_3$, $C_2H_5$, $C_3H_7$, cyclopropyl, etc. In some embodiments, $R^c$ is H.

With respect to any relevant formula or structural depiction herein, such as Formula 1, Formula 2, Formula 3, or Formula 4, $R^1$ is $R^a$, $OR^2$ or $NR^2R^3$. In some embodiments, $R^1$ is optionally substituted phenyl. In some embodiments, $R^1$ is unsubstituted phenyl. In some embodiments, $R^1$ is optionally substituted naphthyl. In some embodiments, $R^1$ is unsubstituted naphthyl.

In some embodiments, $R^1$ is

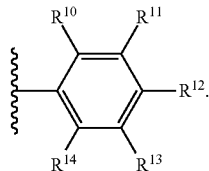

In some embodiments, $R^1$ is

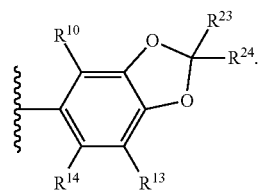

In some embodiments, $R^1$ is

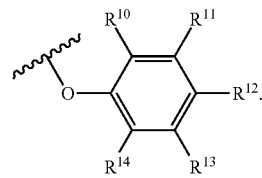

In some embodiments, $R^1$ is

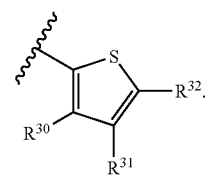

In some embodiments, $R^1$ is

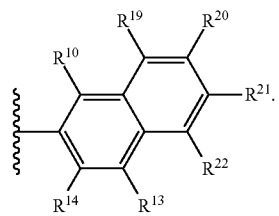

In some embodiments, $R^1$ is

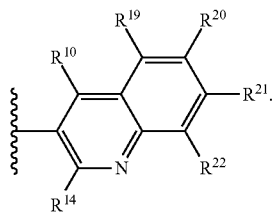

In some embodiments, $R^1$ is

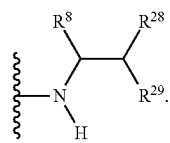

With respect to any relevant structural feature herein, $R^2$ may be $R^a$, $COR^a$, or $SO_2R^a$. In some embodiments, $R^2$ may be H, methyl, ethyl, a propyl (e.g. n-propyl, isopropyl, etc.), cyclopropyl, a butyl, cyclobutyl or an isomer thereof, a pentyl, cyclopentyl or an isomer thereof, a hexyl, a cyclohexyl or an isomer thereof, etc. In some embodiments, $R^2$ is H.

With respect to any relevant structural feature herein, $R^3$ may be $R^a$, $COR^a$, or $SO_2R^a$. In some embodiments, $R^3$ may be H, methyl, ethyl, a propyl (e.g. n-propyl, isopropyl, etc.), cyclopropyl, a butyl, cyclobutyl or an isomer thereof, a pentyl, cyclopentyl or an isomer thereof, a hexyl, a cyclohexyl or an isomer thereof, etc. In some embodiments, $R^3$ is H.

With respect to any relevant structural feature herein, each $R^4$ may independently be $R^2$, $OR^a$, $COR^a$, $CO_2R^a$, $OCOR^a$, $CONR^2R^3$, $NR^2R^3$, $NR^bCOR^a$, $SR^a$, $SOR^a$, $SO_2R^a$, $SO_2NR^aR^b$, $NCOR^a$, halogen, trihalomethyl, CN, S=O, nitro, or $C_{2-5}$ heteroaryl. In some embodiments, $R^4$ is H.

Generally $R^5$ and $R^8$-$R^{32}$, may be H or any substituent, such as a substituent having from 0 to 6 carbon atoms and from 0 to 5 heteroatoms independently selected from: O, N, S, F, Cl, Br, and I, and/or having a molecular weight of 15 g/mol to 300 g/mol. Any of $R^5$ and $R^8$-$R^{32}$ may comprise: a) 1 or more alkyl moieties optionally substituted with, or optionally connected by, b) 1 or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or may be a substituent having no alkyl portion, such as F, Cl, Br, I, $NO_2$, CN, $NH_2$, OH, COH, $CO_2H$, etc.

With respect to any relevant structural feature herein, In some embodiments, $R^5$ may be $R^a$, $COR^a$, $SO_2R^a$, or may not be present. Some non-limiting examples of $R^5$ may include H or $C_{1-3}$ alkyl, such as $CH_3$, $C_2H_5$, $C_7$, cyclopropyl, etc. In some embodiments, $R^5$ may be $CH_3$. In some embodiments, $R^5$ is H.

With respect to any relevant formula or structural depiction above, some non-limiting examples of $R^8$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, CN, $NO_2$, F, Cl, Br, I, or $C_{2-5}$ heterocyclyl. In some embodiments, $R^8$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C≡CH$, or $NO_2$. In some embodiments, $R^8$ is H.

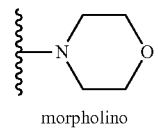
morpholino

With respect to any relevant formula or structural depiction above, some non-limiting examples of $R^9$ may include $R^b$, $COR^b$, $CO_2R^b$, $CONR^bR^c$, $NR^bCOR^c$, $SO_2NR^bR^c$, $CF_3$, CN, or $C_{2-5}$ heterocyclyl. In some embodiments, $R^9$ is H, $CH_3$, $CH_2CH_3$, $SO_2NH_2$, or $CH_2C≡CH$. In some embodiments, $R^9$ is H, $CH_3$, $CH_2CH_3$, $CH_2CH_2CH_3$, $CH_2CH=CH_2$, or $CH_2C≡CH$. In some embodiments, $R^9$ is $CH_2C≡CH$. In some embodiments, $R^9$ is H.

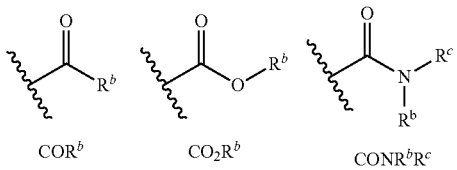

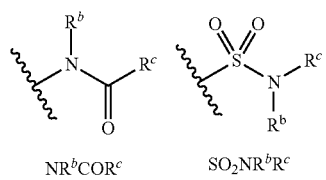

With respect to any relevant formula or structural depiction above, some non-limiting examples of $R^{10}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, CN, $NO_2$, F, Cl, Br, I, or $C_{2-5}$ heterocyclyl. In some embodiments, $R^{10}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C≡CH$, or $NO_2$. In some embodiments, $R^{10}$ is H.

With respect to any relevant formula or structural depiction above, some non-limiting examples of $R^{11}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, CN, $NO_2$, F, Cl, Br, I, or $C_{2-5}$ heterocyclyl. In some embodiments, $R^{11}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C≡CH$, or $NO_2$. In some embodiments, $R^{11}$ is H, Cl or Br. In some embodiments, $R^{11}$ is Cl. In some embodiments, $R^{11}$ is Br. In some embodiments, $R^{11}$ is H.

With respect to any relevant formula or structural depiction above, some non-limiting examples of $R^{12}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, CN, $NO_2$, F, Cl, Br, I, or $C_{2-5}$ heterocyclyl. In some embodiments, $R^{12}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C≡CH$, or $NO_2$. In some embodiments, $R^{12}$ is H, Cl, or $SO_2NH_2$. In some embodiments, $R^{12}$ is H. In some embodiments, $R^{12}$ is Cl. In some embodiments, $R^{12}$ is $SO_2NH_2$. In some embodiments, $R^{12}$ is H.

In some embodiments, $R^{11}$ and $R^{12}$ are together:

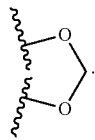 [SMILES: *OCO*]

With respect to any relevant formula or structural depiction above, some non-limiting examples of $R^{13}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, Cl, Br, I, or $C_{2-5}$ heterocyclyl. In some embodiments, $R^{13}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{13}$ is H or Cl. In some embodiments, $R^{13}$ is H. In some embodiments, $R^{13}$ is Cl. In some embodiments, $R^{11}$ and $R^{13}$ are Cl.

With respect to any relevant formula or structural depiction above, some non-limiting examples of $R^{14}$ may include $R^b$, $OR^b$, $SR^b$, $COR^b$, $CO_2R^b$, $OCOR^b$, $NR^bR^c$, $CONR^bR^c$, $NR^bCOR^c$, $CF_3$, $CN$, $NO_2$, F, Cl, Br, or I. In some embodiments, $R^{14}$ is H, $CH_3$, $CH_2CH_3$, Cl, Br, OH, $OCH_3$, $SCH_3$, $NH_2$, $NHCH_3$, $N(CH_3)_2$, $CH_2C\equiv CH$, or $NO_2$. In some embodiments, $R^{14}$ is H.

In some embodiments, $R^{10}$ and $R^{14}$ are H. In some embodiments, $R^{10}$, $R^{12}$, and $R^{14}$ are H. In some embodiments, $R^{10}$, $R^{13}$, and $R^{14}$ are H. In some embodiments, $R^{10}$, $R^{11}$, $R^{13}$, and $R^{14}$ are H. In some embodiments, $R^{10}$, $R^{11}$, $R^{12}$, and $R^{14}$ are H. In some embodiments, $R^{10}$, $R^{11}$, $R^{12}$, $R^{13}$, and $R^{14}$ are H.

With respect to any relevant formula or structural depiction above, some non-limiting examples of $R^{16}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, Cl, Br, or $C_{2-5}$ heterocyclyl. In some embodiments, $R^{16}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{16}$ is H.

With respect to any relevant formula or structural depiction above, some non-limiting examples of $R^{17}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, Cl, Br, I, or $C_{2-5}$ heterocyclyl. In some embodiments, $R^{17}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{17}$ is H.

With respect to any relevant formula or structural depiction above, some non-limiting examples of $R^{18}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, Cl, Br, I, or $C_{2-5}$ heterocyclyl. In some embodiments, $R^{18}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{18}$ is H or $CH_3$. In some embodiments, $R^{18}$ is H. In some embodiments, $R^{18}$ is $CH_3$. In some embodiments, $R^{18}$ is H.

With respect to any relevant formula or structural depiction above, some non-limiting examples of $R^{19}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, Cl, Br, or $C_{2-5}$ heterocyclyl. In some embodiments, $R^{19}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{19}$ is H.

With respect to any relevant formula or structural depiction above, some non-limiting examples of $R^{20}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, Cl, Br, I, or $C_{2-5}$ heterocyclyl. In some embodiments, $R^{20}$ is H, $CH_3$, $CH_2CH_3$, Cl, Br, OH, $OCH_3$, $SCH_3$, $NH_2$, $NHCH_3$, $N(CH_3)_2$, $SO_2NH_2$, $CH_2C\equiv CH$, or $NO_2$. In some embodiments, $R^{20}$ is H.

With respect to any relevant formula or structural depiction above, some non-limiting examples of $R^{21}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, Cl, Br, I, or $C_{2-5}$ heterocyclyl. In some embodiments, $R^{21}$ is H, $CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{21}$ is H.

With respect to any relevant formula or structural depiction above, some non-limiting examples of $R^{22}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, Cl, Br, I, or $C_{2-5}$ heterocyclyl. In some embodiments, $R^{22}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, or $NO_2$. In some embodiments, $R^{22}$ is H.

In some embodiments, $R^{19}$, $R^{20}$, $R^{21}$, and $R^{22}$ are H.

With respect to any relevant formula or structural depiction above, some non-limiting examples of $R^{23}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, Cl, Br, I, or $C_{2-5}$ heterocyclyl. In some embodiments, $R^{23}$ is H, $CH_3$, $CH_2CH_3$, Cl, Br, OH, $OCH_3$, $SCH_3$, $NH_2$, $NHCH_3$, $N(CH_3)_2$, $SO_2NH_2$, $CH_2C\equiv CH$, or $NO_2$. In some embodiments, $R^{23}$ is H or $SO_2NH_2$. In some embodiments, $R^{23}$ is H. In some embodiments, $R^{23}$ is $SO_2NH_2$.

With respect to any relevant formula or structural depiction above, some non-limiting examples of $R^{24}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, Cl, Br, I, or $C_{2-5}$ heterocyclyl. In some embodiments, $R^{24}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, or $NO_2$. In some embodiments, be $R^{24}$ may H.

In some embodiments, $R^{23}$ and $R^{24}$ are H.

With respect to any relevant formula or structural depiction above, some non-limiting examples of $R^{25}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, $CN$, $NO_2$, F, or $C_{2-5}$ heterocyclyl. In some embodiments, $R^{25}$ is H, $CH_3$, $CH_2CH_3$, $N(CH_3)_2$, $SO_2NH_2$, morpholino, $CH_2C\equiv CH$, or $NO_2$. In some embodiments, $R^{25}$ is $CH_3$ or H. In some embodiments, $R^{25}$ is H.

With respect to any relevant formula or structural depiction above, some non-limiting examples of $R^{26}$ may include $R^b$, $CF_3$, $CN$, or $NO_2$. In some embodiments, $R^{26}$ is H, $CH_3$, or $CH_2CH_3$. In some embodiments, $R^{26}$ is H.

With respect to any relevant formula or structural depiction above, some non-limiting examples of $R^{27}$ may include $R^b$, $OR^b$, $SR^b$, $COR^b$, $CO_2R^b$, $CONR^bR^c$, $SO_2NR^bR^c$, $CF_3$, $CN$, $NO_2$, F, Cl, Br, I, or $C_{2-5}$ heterocyclyl. In some embodiments, $R^{27}$ is H, $CH_3$, $CH_2CH_3$, Cl, Br, OH, $OCH_3$, $SCH_3$, $SO_2NH_2$, $CH_2C\equiv CH$, or $NO_2$. In some embodiments, $R^{27}$ is H, $(CH_2)_3CH_3$, $CH_2CH_2OCH_3$, $CH_2CH_2N(CH_3)_2$, $CH_2CH_2$-morpholino, or $CH_2CH_2SCH_3$. In some embodiments, $R^{27}$ is H. In some embodiments, $R^{27}$ is $(CH_2)_3CH_3$. In some embodiments, $R^{27}$ is $CH_2CH_2OCH_3$. In some embodiments, $R^{27}$ is $CH_2CH_2N(CH_3)_2$. In some embodiments, $R^{27}$ is $CH_2CH_2$-morpholino. In some embodiments, $R^{27}$ is $CH_2CH_2SCH_3$.

With respect to any relevant formula or structural depiction above, some non-limiting examples of $R^{28}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, CN, $NO_2$, F, Cl, Br, I, or $C_{2-5}$ heterocyclyl. In some embodiments, $R^{28}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{28}$ is H, $CH_2CH_3$, $OCH_3$, $N(CH_3)_2$, morpholino, or $SCH_3$. In some embodiments, $R^{28}$ is H. In some embodiments, $R^{28}$ is $CH_2CH_3$. In some embodiments, $R^{28}$ is $OCH_3$. In some embodiments, $R^{28}$ is $CN(CH_3)_2$. In some embodiments, $R^{28}$ is morpholino. In some embodiments, $R^{28}$ is $SCH_3$.

With respect to any relevant formula or structural depiction above, some non-limiting examples of $R^{29}$ may include $R^b$, $OR^b$, $SR^b$, $CF_3$, CN, $NO_2$, F, Cl, Br, I, or $C_{2-5}$ heterocyclyl. In some embodiments, $R^{29}$ is H, $CH_3$, or $CH_2CH_3$. In some embodiments, $R^{29}$ is H.

In some embodiments, $R^8$ and $R^{29}$ are H.

With respect to any relevant formula or structural depiction above, some non-limiting examples of $R^{30}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, CN, $NO_2$, F, Cl, Br, or I. In some embodiments, $R^{30}$ is H, $CH_3$, $CH_2CH_3$, Cl, Br, OH, $OCH_3$, $SCH_3$, $NH_2$, $NHCH_3$, $N(CH_3)_2$, $SO_2NH_2$, $CH_2C\equiv CH$, or $NO_2$. In some embodiments, $R^{30}$ is H.

With respect to any relevant formula or structural depiction above, some non-limiting examples of $R^{31}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, CN, $NO_2$, F, Cl, Br, I, or $C_{2-5}$ heterocyclyl. In some embodiments, $R^{31}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{31}$ is H.

With respect to any relevant formula or structural depiction above, some non-limiting examples of $R^{32}$ may include $R^b$, $OR^b$, $SR^b$, $COR^b$, $CO_2R^b$, $OCOR^b$, $NR^bR^c$, $CONR^bR^c$, $NR^bCOR^c$, $SO_2NR^bR^c$, $CF_3$, CN, $NO_2$, F, Cl, Br, I, or $C_{2-5}$ heterocyclyl. In some embodiments, $R^{32}$ is H, $CH_3$, $CH_2CH_3$, Cl, Br, OH, $OCH_3$, $SCH_3$, $NH_2$, $NHCH_3$, $N(CH_3)_2$, $SO_2NH_2$, morpholino, $CH_2C\equiv CH$, or $NO_2$. In some embodiments, $R^{32}$ is H or $NO_2$. In some embodiments, $R^{32}$ is H. In some embodiments, $R^{32}$ is $NO_2$.

In some embodiments, $R^{30}$, $R^{31}$, and $R^{32}$ are H. In some embodiments, $R^{31}$ and $R^{32}$ are H.

$NHCH_3$, $N(CH_3)_2$, $SO_2NH_2$, morpholino, $CH_2C\equiv CH$, or $NO_2$. In some embodiments, $R^{33}$ is H.

In another embodiment disclosed herein the compound is (the "KIN1000" compound)

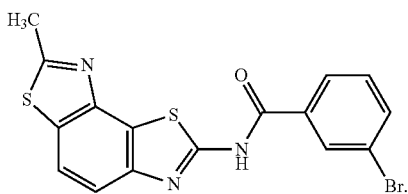 [SMILES: Cc1nc2c(ccc3nc(NC(=O)c4cccc(Br)c4)sc32)s1]

Unless otherwise indicated, any reference to a compound herein by structure, formula, name or any other means, includes pharmaceutically acceptable salts, such as sodium, potassium, and ammonium salts; prodrugs, such as ester prodrugs; alternate solid forms, such as polymorphs, solvates, hydrates, etc.; tautomers; or, any other chemical species that may rapidly convert to a compound described herein under conditions in which the compounds are used as described herein.

Unless stereochemistry is unambiguously depicted, any structure, formula or name for a compound can refer to any stereoisomer or any mixture of stereoisomers of the compound.

As used herein, the term "functional group" refers to an atom or a group of atoms that have similar chemical properties whenever they occur in different compounds, and as such the functional group defines the characteristic physical and chemical properties of families of organic compounds.

Unless otherwise indicated, when any compound or chemical structural feature (collectively referred to herein as a "compound"), such as for example alkyl, aryl, etc., is referred to as being "optionally substituted," that compound can have no substituents (in which case it is "unsubstituted"), or it can include one or more substituents (in which case it is "substituted"). The term "substituent" has the ordinary meaning known to one of ordinary skill in the art. In some embodiments, the substituent may be an ordinary organic moiety known in the art, which can have a molecular weight (e.g., the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, the substituent comprises: 0-30, 0-20, 0-10, or 0-5 carbon (C) atoms; and/or 0-30, 0-20, 0-10, or 0-5 heteroatoms including N, O, S, Si, F, Cl, Br, or I; provided that the substituent comprises at least one atom including C, N, O, S, Si, F, Cl, Br, or I in a substituted compound. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc. For convenience, the term "molecular weight" is used with respect to a moiety or part of a molecule to indicate the sum of the atomic masses of the atoms in the moiety or part of a molecule, even though it may not be a complete molecule.

As used herein, the term "hydrocarbyl" has the broadest meaning generally understood in the art, and can include a moiety composed of carbon and hydrogen. Some examples can include alkyl, alkenyl, alkynyl, aryl, etc., and combinations thereof, and can be linear, branched, cyclic, or a combination thereof. Hydrocarbyl can be bonded to any other number of moieties (for example, can be bonded to one other group, such as —$CH_3$, —CH=$CH_2$, etc.; two other groups, such as -phenyl-, —C≡C—, etc.; or any number of other groups) that the structure can bear, and in some embodiments, can contain from one to thirty-five carbon atoms. Examples of hydrocarbyl groups include but are not limited to $C_1$ alkyl, $C_2$ alkyl, $C_2$ alkenyl, $C_2$ alkynyl, $C_3$ alkyl, $C_3$ alkenyl, $C_3$ alkynyl, $C_4$ alkyl, $C_4$ alkenyl, $C_4$ alkynyl, $C_5$ alkyl, $C_5$ alkenyl, $C_5$ alkynyl, $C_6$ alkyl, $C_6$ alkenyl, $C_6$ alkynyl, phenyl, etc.

As used herein the term "alkyl" has the broadest meaning generally understood in the art, and can include a moiety composed of carbon and hydrogen containing no double or triple bonds and not having any cyclic structure. Alkyl can be linear alkyl, branched alkyl, cycloalkyl, or a combination thereof, and in some embodiments, can contain from one to thirty-five carbon atoms. In some embodiments, alkyl can include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. isopropyl), $C_4H_9$ (e.g., branched butyl isomers), $C_5H_{11}$ (e.g., branched pentyl isomers), $C_6H_{13}$ (e.g., branched hexyl isomers), $C_7H_{15}$ (e.g., branched heptyl isomers), etc.; $C_{3-10}$ cycloalkyl, such as $C_3H_5$ (e.g. cyclopropyl), $C_4H_7$ (e.g., cyclobutyl isomers such as cyclobutyl, methylcyclopropyl, etc.), $C_5H_9$ (e.g., cyclopentyl isomers such as cyclopentyl, methylcyclobutyl, dimethylcyclopropyl, etc.) $C_6H_{11}$ (e.g., cyclohexyl isomers), $C_7H_{13}$ (e.g., cycloheptyl isomers), etc.; and the like.

The terms "alkyl," "alkenyl" and "alkynyl" refer to substituted and unsubstituted alkyls, alkenyls and alkynyls, respectively. An alkyl group can be optionally substituted as defined herein.

Substituted alkyls, alkenyls and alkynyls refers to alkyls, alkenyls and alkynyls substituted with one to five substituents including H, lower alkyl, aryl, alkenyl, alkynyl, arylalkyl, alkoxy, aryloxy, arylalkoxy, alkoxyalkylaryl, alkylamino, arylamino, $NH_2$, OH, CN, $NO_2$, $OCF_3$, $CF_3$, F, 1-amidine, 2-amidine, alkylcarbonyl, morpholinyl, piperidinyl, dioxanyl, pyranyl, heteroaryl, furanyl, thiophenyl, tetrazolo, thiazolyl, isothiazolyl, imidazolyl, thiadiazolyl, thiadiazole S-oxide, thiadiazole S,S-dioxide, pyrazolo, oxazolyl, isoxazolyl, pyridinyl, pyrimidinyl, quinolinyl, isoquinolinyl, SR, SOR, $SO_2R$, $CO_2R$, COR, CONR'R", CSNR'R" and $SO_nNR'R"$.

As used herein, either alone or in combination, the term "alkynyl" refers to a functional group comprising a straight-chain or branched-chain hydrocarbon containing from 2 to 20 carbon atoms and having one or more carbon-carbon triple bonds and not having any cyclic structure. An alkynyl group may be optionally substituted as defined herein. Examples of alkynyl groups include, without limitation, ethynyl, propynyl, hydroxypropynyl, butynyl, butyn-1-yl, butyn-2-yl, 3-methylbutyn-1-yl, pentynyl, pentyn-1-yl, hexynyl, hexyn-2-yl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, and the like.

The term "alkylene" as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

As used herein, either alone or in combination, the term "alkylcarbonyl" or "alkanoyl" refers to a functional group comprising an alkyl group attached to the parent molecular moiety through a carbonyl group. Examples of alkylcarbonyl groups include, without limitation, methylcarbonyl, ethylcarbonyl, and the like.

As used herein, either alone or in combination, the term "heteroalkyl" refers to a functional group comprising a straight-chain or branched-chain hydrocarbon containing from 1 to 20 atoms linked exclusively by single bonds, where at least one atom in the chain is a carbon and at least one atom in the chain is O, S, N, or any combination thereof. The heteroalkyl group can be fully saturated or contain from 1 to 3 degrees of unsaturation. The non-carbon atoms can be at any interior position of the heteroalkyl group, and up to two non-carbon atoms may be consecutive, such as, e.g., —$CH_2$—NH—$OCH_3$. In addition, the non-carbon atoms may optionally be oxidized and the nitrogen may optionally be quaternized.

As used herein, either alone or in combination, the term "alkyloxy" or "alkoxy" refers to a functional group comprising an alkyl ether group. Examples of alkoxys include, without limitation, methoxy, ethoxy, n-propoxy, isopropoxy, n-butoxy, iso-butoxy, sec-butoxy, tert-butoxy, and the like.

As used herein, either alone or in combination, the term "hydroxy" refers to the functional group hydroxyl (—OH).

As used herein, either alone or in combination, the term "carboxyl" or "carboxy" refers to the functional group —C(=O)OH or the corresponding "carboxylate" anion —C(=O)O—. Examples include, without limitation, formic acid, acetic acid, oxalic acid, benzoic acid. An "O-carboxyl" group refers to a carboxyl group having the general formula RCOO, wherein R is an organic moiety or group. A "C-carboxyl" group refers to a carboxyl group having the general formula COOR, wherein R is an organic moiety or group.

As used herein, either alone or in combination, the term "oxo" refers to the functional group =O.

As used herein, the term "carbocyclic" has the broadest meaning generally understood in the art, and includes a ring or ring system wherein the ring atoms are all carbon. Examples include, but are not limited to, phenyl, naphthyl, anthracenyl, cycloalkyl, cycloalkenyl, cycloalkynyl, etc., and combinations thereof.

As used herein, the term "heterocyclic" has the broadest meaning generally understood in the art, and includes a ring or ring system wherein at least one of the ring atoms is not carbon, such as N, O, S, etc. Examples include, but are not limited to, heteroaryl, cycloheteroalkyl, cycloheteroalkenyl, cycloheteroalkynyl, etc., and combinations thereof.

As used herein, either alone or in combination, the term "cycloalkyl," "carbocyclicalkyl" and "carbocyclealkyl" refers to a functional group comprising a substituted or unsubstituted non-aromatic hydrocarbon with a non-conjugated cyclic molecular ring structure of 3 to 12 carbon atoms linked exclusively with carbon-carbon single bonds in the carbon ring structure. A cycloalkyl group can be monocyclic, bicyclic or polycyclic, and may optionally include one to three additional ring structures, such as, e.g., an aryl, a heteroaryl, a cycloalkenyl, a heterocycloalkyl, or a heterocycloalkenyl.

As used herein, either alone or in combination, the term "lower cycloalkyl" refers to a functional group comprising a monocyclic substituted or unsubstituted non-aromatic hydrocarbon with a non-conjugated cyclic molecular ring structure of 3 to 6 carbon atoms linked exclusively with carbon-carbon single bonds in the carbon ring structure. Examples of lower cycloalkyl groups include, without limitation, cyclopropyl, cyclobutyl, cyclopentyl, and cyclohexyl.

As used herein the term "aryl" has the broadest meaning generally understood in the art, and can include an aromatic ring or aromatic ring system. An aryl group can be monocyclic, bicyclic or polycyclic, and may optionally include one to three additional ring structures; such as, for example, a cycloalkyl, a cycloalkenyl, a heterocycloalkyl, a heterocycloalkenyl, or a heteroaryl. The term "aryl" includes, without limitation, phenyl (benzenyl), thiophenyl, indolyl, naphthyl, tolyl, xylyl, anthracenyl, phenanthryl, azulenyl, biphenyl, naphthalenyl, 1-methylnaphthalenyl, acenaphthenyl, acenaphthylenyl, anthracenyl, fluorenyl, phenalenyl, phenanthrenyl, benzo[a]anthracenyl, benzo[c]phenanthrenyl, chrysenyl, fluoranthenyl, pyrenyl, tetracenyl (naphthacenyl), triphenylenyl, anthanthrenyl, benzopyrenyl, benzo[a]pyrenyl, benzo[e]fluoranthenyl, benzo[ghi]perylenyl, benzo[j]fluoranthenyl, benzo[k]fluoranthenyl, corannulenyl, coronenyl, dicoronylenyl, helicenyl, heptacenyl, hexacenyl, ovalenyl, pentacenyl, picenyl, perylenyl, tetraphenylenyl, etc.

Additionally, as used herein, either alone or in combination, the term "aryl," "hydrocarbyl aryl" or "aryl hydrocarbon" can refer to a functional group comprising a substituted or unsubstituted aromatic hydrocarbon with a conjugated cyclic molecular ring structure of 3 to 12 carbon atoms. Substituted aryl refers to aryls substituted with one to five substituents including H, lower alkyl, aryl, alkenyl, alkynyl, arylalkyl, alkoxy, aryloxy, arylalkoxy, alkoxyalkylaryl, alkylamino, arylamino, $NH_2$, OH, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, SR, SOR, $SO_2R$, $CO_2R$, COR, CONR'R", CSNR'R", $SO_n$-NR'R", etc.

As used herein, either alone or in combination, the term "lower aryl" refers to a functional group comprising a substituted or unsubstituted aromatic hydrocarbon with a conjugated cyclic molecular ring structure of 3 to 6 carbon atoms. Examples of lower aryl groups include, without limitation, phenyl and naphthyl.

As used herein, either alone or in combination, the term "heteroaryl" refers to a functional group comprising a substituted or unsubstituted aromatic hydrocarbon with a conjugated cyclic molecular ring structure of 3 to 12 atoms, where at least one atom in the ring structure is a carbon and at least one atom in the ring structure is O, S, N, or any combination thereof. A heteroaryl group can be monocyclic, bicyclic or polycyclic, and may optionally include one to three additional ring structures, such as, e.g., an aryl, a cycloalkyl, a cycloalkenyl, a heterocycloalkyl, or a heterocycloalkenyl. Examples of heteroaryl groups include, without limitation, acridinyl, benzidolyl, benzimidazolyl, benzisoxazolyl, benzodioxinyl, dihydrobenzodioxinyl, benzodioxolyl, 1,3-benzodioxolyl, benzofuryl, benzoisoxazolyl, benzopyranyl, benzothiophenyl, benzo[c]thiophenyl, benzotriazolyl, benzoxadiazolyl, benzoxazolyl, benzothiadiazolyl, benzothiazolyl, benzothienyl, carbazolyl, chromonyl, cinnolinyl, dihydrocinnolinyl, coumarinyl, dibenzofuranyl, furopyridinyl, furyl, indolizinyl, indolyl, dihydroindolyl, imidazolyl, indazolyl, isobenzofuryl, isoindolyl, isoindolinyl, dihydroisoindolyl, isoquinolyl, dihydroisoquinolinyl, isoxazolyl, isothiazolyl, oxazolyl, oxadiazolyl, phenanthrolinyl, phenanthridinyl, purinyl, pyranyl, pyrazinyl, pyrazolyl, pyridyl, pyrimidinyl, pyridazinyl, pyrrolinyl, pyrrolyl, pyrrolopyridinyl, quinolyl, quinoxalinyl, quinazolinyl, tetrahydroquinolinyl, tetrazolopyridazinyl, tetrahydroisoquinolinyl, thiophenyl, thiazolyl, thiadiazolyl, thienopyridinyl, thienyl, thiophenyl, triazolyl, xanthenyl, and the like.

As used herein, either alone or in combination, the term "lower heteroaryl" refers to a functional group comprising a monocyclic or bicyclic, substituted or unsubstituted aromatic hydrocarbon with a conjugated cyclic molecular ring structure of 3 to 6 atoms, where at least one atom in the ring structure is a carbon and at least one atom in the ring structure is O, S, N, or any combination thereof.

The phenyl structure associated with some of the embodiments described herein is depicted below. This structure can be unsubstituted, as shown below, or can be substituted such that a substituent can independently be in any position normally occupied by a hydrogen atom when the structure is unsubstituted. Unless a point of attachment is indicated by -|, attachment may occur at any position normally occupied by a hydrogen atom.

Phenyl

Each $R_a$ can independently be H; optionally substituted hydrocarbyl; optionally substituted aryl, such as optionally substituted phenyl or optionally substituted aryl; optionally substituted heteroaryl, such as optionally substituted pyridinyl, optionally substituted furyl, optionally substituted thienyl, etc. In some embodiments, each $R_a$ can independently be H, or $C_{1-12}$ alkyl, including: linear or branched alkyl having the formula $C_aH_{a+1}$, or cycloalkyl having the formula $C_aH_{a-1}$, wherein a is 1, 2, 3, 4, 5, 6, 7, 8, 9, 10, 11, or 12, such as linear or branched alkyl of the formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of the formula: $C_3H_5$, $C_4H_7$, $C_5H_9$, $C_6H_{11}$, $C_7H_{13}$, $C_5H_{15}$, $C_9H_{17}$, $C_{10}H_{19}$, etc.

The term "treat" includes one or more of the diagnosis, cure, mitigation, vaccination, augmentation of a therapy or prevention of disease in man or other animals As used herein, the term "vertebrate" includes all living vertebrates such as, without limitation, mammals, humans, birds, dogs, cats, livestock, farm animals, free-range herds, etc.

Many RNA viruses share biochemical, regulatory, and signaling pathways. These viruses include but are not limited to influenza virus (including avian and swine isolates), respiratory syncytial virus, Hepatitis C virus, West Nile virus, SARS-coronavirus, poliovirus, measles virus, Dengue virus, yellow fever virus, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, and the Kyasanur forest disease virus. The compounds and methods disclosed herein can be used to treat these viruses.

Relevant taxonomic families of RNA viruses include, without limitation, Arenaviridae, Astroviridae, Birnaviridae, Bromoviridae, Bunyaviridae, Caliciviridae, Closteroviridae, Comoviridae, Cystoviridae, Flaviviridae, Flexiviridae, Hepevirus, Leviviridae, Luteoviridae, Mononegavirales, Mosaic Viruses, Nidovirales, Nodaviridae, Orthomyxoviridae, Paramyxoviridae, Picobirnavirus, Picornaviridae, Potyviridae, Reoviridae, Retroviridae, Sequiviridae, Tenuivirus, Togaviridae, Tombusviridae, Totiviridae, and Tymoviridae. The compounds and methods disclosed herein can be used to treat viruses within these families of viruses as part of a pharmaceutically acceptable drug formulation. Other relevant virus families include, without limitation, Hepadnaviridae, Herpesviridae, and Papillomaviridae.

Particular embodiments provide for pharmaceutical compositions comprising the compounds, alone or in combination with an antigen, for the purpose of treating and/or preventing disease in an animal including a vertebrate animal. As such, in some embodiments the pharmaceutical compositions can be used as vaccines.

The disclosure provides for the use of the compounds as adjuvants.

The compounds and methods disclosed herein can be additive or synergistic with other therapies currently in development or use. For example, ribavirin and interferon-α provide an effective treatment for HCV infection when used in combination. Their efficacy in combination can exceed the efficacy of either drug product when used alone. The compositions of the disclosure can be administered alone or in combination or conjunction with interferon, ribavirin and/or a variety of small molecules that are being developed against both viral targets (viral proteases, viral polymerase, assembly of viral replication complexes) and host targets (host proteases required for viral processing, host kinases required for phosphorylation of viral targets such as NS5A, and inhibitors of host factors required to efficiently utilize the viral internal ribosome entry site, or IRES).

The compounds and methods disclosed herein could be used in combination or conjunction with, without limitation, adamantane inhibitors, neuraminidase inhibitors, alpha interferons, non-nucleoside or nucleoside polymerase inhibitors, NS5A inhibitors, antihistamines, protease inhibitors, helicase inhibitors, P7 inhibitors, entry inhibitors, IRES inhibitors, immune stimulators, HCV replication inhibitors, cyclophilin A inhibitors, $A_3$ adenosine agonists, and micro-RNA suppressors.

Cytokines that could be administered in combination or conjunction with the compounds and methods disclosed herein include, without limitation, IL-2, IL-12, IL-23, IL-27, or IFN-γ. New HCV drugs that are or will be available for potential administration in combination or conjunction with the compounds and methods disclosed herein include, without limitation, ACH-1625 (Achillion); Glycosylated interferon (Alios Biopharma); ANA598, ANA773 (Anadys Pharm); ATI-0810 (Arisyn Therapeutics); AVL-181 (Avila Therapeutics); LOCTERON® (Biolex); CTS-1027 (Conatus); SD-101 (Dynavax Technologies); Clemizole (Eiger Biopharmaceuticals); GS-9190 (Gilead Sciences); GI-5005 (Globallmmune BioPharma); Resiquimod/R-848 (Graceway Pharmaceuticals); Albinterferon alpha-2b (Human Genome Sciences); IDX-184, IDX-320, IDX-375 (Idenix); IMO-2125 (Idera Pharmaceuticals); INX-189 (Inhibitex); ITCA-638 (Intarcia Therapeutics); ITMN-191/RG7227 (Intermune); ITX-5061, ITX-4520 (iTherx Pharmaceuticals); MB11362 (Metabasis Therapeutics); Bavituximab (Peregrine Pharmaceuticals); PSI-7977, RG7128, PSI-938 (Pharmasset); PHX1766 (Phenomix); Nitazoxanide/ALINIA® (Romark Laboratories); SP-30 (Samaritan Pharmaceuticals); SCV-07 (SciClone); SCY-635 (Scynexis); TT-033 (Tacere Therapeutics); Viramidine/taribavirin (Valeant Pharmaceuticals); Telaprevir, VCH-759, VCH-916, VCH-222, VX-500, VX-813 (Vertex Pharmaceuticals); and PEG-INF Lambda (Zymogenetics).

New influenza and West Nile virus drugs that are or will be available for potential administration in combination or conjunction with the compounds and methods disclosed herein include, without limitation, neuraminidase inhibitors (Peramivir, Laninamivir); triple therapy—neuraminidase inhibitors ribavirin, amantadine (ADS-8902); polymerase inhibitors (Favipiravir); reverse transcriptase inhibitor (ANX-201); inhaled chitosan (ANX-211); entry/binding inhibitors (Binding Site Mimetic, FLUCIDE™ (NanoViricides, West Haven, Conn.); entry inhibitor (FLUDASE® (NexBio, San Diego, Calif.); fusion inhibitor, (MGAWN1 for West Nile); host cell inhibitors (lantibiotics); cleavage of RNA genome (RNAi, RNAse L); immune stimulators (Interferon, Alferon-LDO; Neurokinin1 agonist, Homspera, Interferon Alferon N for West Nile); and TG21.

Other drugs for treatment of influenza and/or hepatitis that are available for potential administration in combination or conjunction with the compounds and methods disclosed herein include, without limitation:

TABLE 1

Hepatitis and influenza drugs

| Branded Name | Generic Name | Approved Indications |
| --- | --- | --- |
| PEGASYS ® (Genentech, South San Francisco, California) | PEGinterferon alfa-2a | Hepatitis C, Hepatitis B |
| PEGINTRON ® (Merck, Whitehouse Station, New Jersey) | PEGinterferon alfa-2b | Hepatitis C |
| COPEGUS ® (Roche Pharmaceuticals, Nutley, New Jersey) | Ribavirin | Hepatitis C |
| REBETOL ® (Schering Plough, Kenilworth, New Jersey) | Ribavirin | Hepatitis C |
| — | Ribavirin | Hepatitis C |
| TAMIFLU ® (Roche Pharmaceuticals, Nutley, New Jersey) | Oseltamivir | Influenza A, B, C |
| RELENZA ® (GlaxoSmithKline, London, UK) | Zanamivir | Influenza A, B, C |
| — | Amantadine | Influenza A |
| — | Rimantadine | Influenza A |

These agents can be incorporated as part of the same pharmaceutical composition or can be administered separately from the compounds of the disclosure, either concurrently or in accordance with another treatment schedule.

The compounds and methods disclosed herein can be additive or synergistic with other compounds and methods to enable vaccine development. By virtue of their antiviral and immune enhancing properties, the compounds can be used to affect a prophylactic or therapeutic vaccination. The compounds need not be administered simultaneously or in combination with other vaccine components to be effective. The vaccine applications of the compounds are not limited to the prevention or treatment of virus infection but can encompass all therapeutic and prophylactic vaccine applications due to the general nature of the immune response elicited by the compounds.

As is understood by one of ordinary skill in the art, vaccines can be against viruses, bacterial infections, cancers, etc. and can include one or more of, without limitation, a live attenuated vaccine (LAIV), an inactivated vaccine (IIV; killed virus vaccine), a subunit (split vaccine); a sub-virion vaccine; a purified protein vaccine; or a DNA vaccine. Appropriate adjuvants include one or more of, without limitation, water/oil emulsions, non-ionic copolymer adjuvants, e.g., CRL 1005 (Optivax™; Vaxcel Inc., Norcross, Ga.), aluminum phosphate, aluminum hydroxide, aqueous suspensions of aluminum and magnesium hydroxides, bacterial endotoxins, polynucleotides, polyelectrolytes, lipophilic adjuvants and synthetic muramyl dipeptide (norMDP)

analogs such as N-acetyl-nor-muranyl-L-alanyl-D-isoglutamine, N-acetyl-muranyl-(6-O-stearoyl)-L-alanyl-D-isoglutamine or N-Glycol-muranyl-LalphaAbu-D-isoglutamine (Ciba-Geigy Ltd.).

The pharmaceutical composition comprising a compound of the disclosure can be formulated in a variety of forms; e.g., as a liquid, gel, lyophilized, or as a compressed solid. The preferred form will depend upon the particular indication being treated and discernible by one of ordinary skill in the art. In one embodiment, the disclosed RIG-I agonists include formulations for oral delivery that can be small-molecule drugs that employ straightforward medicinal chemistry processes.

The administration of the formulations of the present disclosure can be performed in a variety of ways, including, but not limited to, orally, subcutaneously, intravenously, intracerebrally, intranasally, transdermally, intraperitoneally, intramuscularly, intrapulmonary, intrathecally, vaginally, rectally, intraocularly, or in any other acceptable manner. The formulations can be administered continuously by infusion, although bolus injection is acceptable, using techniques known in the art, such as pumps (e.g., subcutaneous osmotic pumps) or implantation. In some instances the formulations can be directly applied as a solution or spray.

An example of a pharmaceutical composition is a solution designed for parenteral administration. Although in many cases pharmaceutical solution formulations are provided in liquid form, appropriate for immediate use, such parenteral formulations can also be provided in frozen or in lyophilized form. In the former case, the composition must be thawed prior to use. The latter form is often used to enhance the stability of the active compound contained in the composition under a wider variety of storage conditions, as it is recognized by those of ordinary skill in the art that lyophilized preparations are generally more stable than their liquid counterparts. Such lyophilized preparations are reconstituted prior to use by the addition of one or more suitable pharmaceutically acceptable diluents such as, without limitation, sterile water for injection or sterile physiological saline solution.

Parenterals can be prepared for storage as lyophilized formulations or aqueous solutions by mixing, as appropriate, the compound having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from 2 mM to 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives can be added to retard microbial growth, and are typically added in amounts of 0.2%-1% (w/v). Suitable preservatives for use with the present disclosure include, without limitation, phenol, benzyl alcohol, meta-cresol, methyl paraben, propyl paraben, octadecyldimethylbenzyl ammonium chloride, benzalkonium halides (e.g., benzalkonium chloride, bromide or iodide), hexamethonium chloride, alkyl parabens such as methyl or propyl paraben, catechol, resorcinol, cyclohexanol and 3-pentanol.

Isotonicifiers can be added to ensure isotonicity of liquid compositions and include, without limitation, polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, alpha-monothioglycerol and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active compound weight.

Additional miscellaneous excipients include fillers (e.g., starch), chelating agents (e.g., EDTA), antioxidants (e.g., ascorbic acid, methionine, vitamin E) and cosolvents.

The active ingredient can also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington, The Science and Practice of Pharmacy, 21$^{st}$ Ed., published by Lippincott Williams & Wilkins, A Wolters Kluwer Company, 2005, the teachings of which are incorporated by reference herein.

Parenteral formulations to be used for in vivo administration generally are sterile. This is readily accomplished, for example, by filtration through sterile filtration membranes.

Suitable examples of sustained-release preparations include semi-permeable matrices of solid hydrophobic polymers containing the compound or composition, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the PROLEASE® technology (Alkermes, Cambridge, Mass.) or LUPRON DEPOT® (injectable microspheres composed of lactic acid-glycolic acid copolymer and leuprolide acetate; Abbott Laboratories, Abbott Park, Ill.), and poly-D-(−)-3-hydroxybutyric acid. While polymers such as ethylene-vinyl acetate and lactic acid-glycolic acid enable release of molecules for long periods such as up to or over 100 days, certain hydrogels release compounds for shorter time periods.

Oral administration of the compounds and compositions is one intended practice of the disclosure. For oral administration, the pharmaceutical composition can be in solid or liquid form, e.g., in the form of a capsule, tablet, powder, granule, suspension, emulsion or solution. The pharmaceutical composition is preferably made in the form of a dosage unit containing a given amount of the active ingredient. A suitable daily dose for a human or other vertebrate can vary widely depending on the condition of the patient and other factors, but can be determined by persons of ordinary skill in the art using routine methods.

In solid dosage forms, the active compound can be admixed with at least one inert diluent such as sucrose, lactose, or starch. Such dosage forms can also comprise, as is normal practice, additional substances, e.g., lubricating agents such as magnesium stearate. In the case of capsules, tablets and pills, the dosage forms can also comprise buffering agents. Tablets and pills can additionally be prepared with enteric coatings.

The compounds or compositions can be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, they can be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are known in the pharmaceutical art. The carrier or diluent can include time delay material, such as glyceryl monostearate or glyceryl distearate alone or with a wax, or other materials known in the art.

The present disclosure further includes the use and application of the compounds, compositions and methods herein in vitro in a number of applications including but not limited to developing therapies and vaccines against viral infections, research in modulation of the innate immune response in eukaryotic cells, etc. The compounds, compositions and methods of the present disclosure can also be used in animal models. The results of such in vitro and animal in vivo uses of the compounds, compositions and methods of the present disclosure can, for example, inform their in vivo use in humans, or they can be valuable independent of any human therapeutic or prophylactic use.

EXAMPLES

The Examples below describe the antiviral and pharmacological properties of the disclosed compounds. The Examples are included to demonstrate particular embodiments of the disclosure. It should be appreciated by those of ordinary skill in the art that the techniques disclosed in the Examples represent techniques and compositions discovered by the inventors to function well in the practice of the disclosure, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the disclosure. For example, the Examples below provide in vitro methods for testing the compounds of the disclosure. Other in vitro virus infection models include but are not limited to flaviviruses such as bovine diarrheal virus, West Nile Virus, and GBV-C virus, other RNA viruses such as respiratory syncytial virus, and the HCV replicon systems. Furthermore, any appropriate cultured cell competent for viral replication can be utilized in the antiviral assays.

Example 1. Biological Activity of KIN1000

Luciferase assay to identify active compounds. Cultured human cells that were stably transfected with a luciferase reporter gene coupled with a RIG-I signaling pathway responsive promoter (IFNβ, ISG56, or ISG54 promoter) were seeded and allowed to grow overnight. The compound "KIN1000" was then added and cells were grown in the presence of KIN1000 for 18-20 hours. Steady-Glo luciferase substrate (Promega) was added and luminescence was read on a luminometer (Berthold).

FIG. 1A shows that KIN1000 as described herein was validated by demonstrating dose-dependent induction of the luciferase reporter gene coupled to the promoters for IFNβ ("IFNβ-LUC," left), ISG56 ("ISG56-LUC," center), and ISG54 ("ISG54-LUC," right). Additionally, KIN1000 did not induce a nonspecific promoter (β-actin-LUC, FIG. 1B).

MTS assay to determine cytotoxicity. Cultured human HeLa cells were treated with increasing amounts of compound or equivalent amounts of DMSO diluted in media for 48 hours to see their effect on cell viability. The proportion of viable cells was calculated using a cell viability assay that measures conversion of a tetrazolium compound [3-(4,5-dimethyl-2-yl)-5-(3-carboxymethoxyphenyl)-2-(4-sulfophenyl)-2H-tetrazolium, inner salt; or MTS] to a colored formazan compound in live cells.

The conversion of MTS to formazan was detected in a 96-well microtiter plate reader, and the resulting optical densities plotted directly to estimate cell viability. Cell Titer One (Promega) was the one-step reagent used, as manufacturer's protocol suggested, and cells were incubated for three hours in the presence of reagent before optical density (O.D.) reading was done. Compounds were diluted to final concentrations of 0, 1, 5, 10, and 20 µM in media containing 0.5% DMSO. Negative control wells contained no compound, and positive control for cytotoxicity was examined using 10% DMSO. Each KIN1000 concentration and control was done in triplicate wells. KIN1000 showed no cytotoxicity to multiple cell types (MTS assay, FIG. 1C).

Immunofluorescent cytochemistry assay to determine IRF-3 activation and translocation to the nucleus. The induction of ISG expression mediated by RIG-I is conferred by phosphorylation, dimerization, and nuclear translocation of the IRF-3 transcription factor. Cultured human HeLa cells were treated with increasing amounts of compound or equivalent amounts of DMSO diluted in media for 20 hours. Positive control wells were infected with 100 HA/mL Sendai virus for an equivalent time period. IRF-3 was detected using polyclonal rabbit serum specific to IRF-3 and a secondary antibody conjugated to DyLight® (Pierce Biotechnology, Inc., Rockford, Ill.) 488. KIN1000 shows a dose dependent increase in nuclear-cytoplasmic difference for IRF-3 (FIG. 2A).

Immunofluorescent cytochemistry assay to determine NFκB activation. The innate immune response dependent on RIG-I also activates the NFκB transcription factor and thus increases nuclear levels. Cultured human HeLa cells were treated with increasing amounts of compound or equivalent amounts of DMSO diluted in media for 20 hours. Positive control wells were infected with 100 HA/mL Sendai virus for an equivalent time period. NFκB was detected using monoclonal mouse antibody specific to the p65 subunit of NFκB and a secondary antibody conjugated to DyLight 488.

Quantification of immunofluorescent assays. 96-well plates containing cultured human cells treated with compound and stained for either IRF-3 or NFκB were scanned and quantified using the ArrayScan® instrument and software (Cellomics). Activation of transcription factor was evidenced by increased nuclear intensity normalized for cytoplasmic intensity, or nuclear-cytoplasmic difference. KIN1000 shows a dose dependent increase in nuclear-cytoplasmic difference for NFκB (FIG. 2B).

Other compounds as described herein likewise can be evaluated by the methods described in this example, and other cell types can also be used.

Example 2. Antiviral Activity of KIB1000 Against Influenza WSN Strain

MRCS cells were treated with increasing amounts of KIN1000 12-24 hours prior to infection by influenza virus. The number of infected cells 24 hours after introduction of virus was then quantified by an immunofluorescent assay of viral protein in cells. The KIN1000 compound disclosed herein demonstrated efficient activity against influenza virus strain WSN. FIG. 3 shows that MRCS cells treated with increasing amounts of KIN1000 showed a dose-dependent decrease in infection by influenza virus.

Example 3. Ex Vivo Immune Stimulatory Activity of KIN1000

The activity of KIN1000 in primary immune cells was assayed to determine whether KIN1000 stimulates immune responses. Cultured human primary dendritic cells were treated with 0, 1, or 10 µM of KIN1000 for 24 hours. Supernatant from treated wells was isolated and tested for levels of cytokine protein. Cytokines were detected using specific antibodies conjugated to magnetic beads and a secondary antibody that reacts with Streptavidin/Phycoerythrin to produce a fluorescent signal. The bound beads were detected and quantified using the Magpix® (Luminex Corp.) instrument, although similar techniques as are known in the art may be used to measure fluorescent protein production, such as for example an ELISA.

Figure 4:
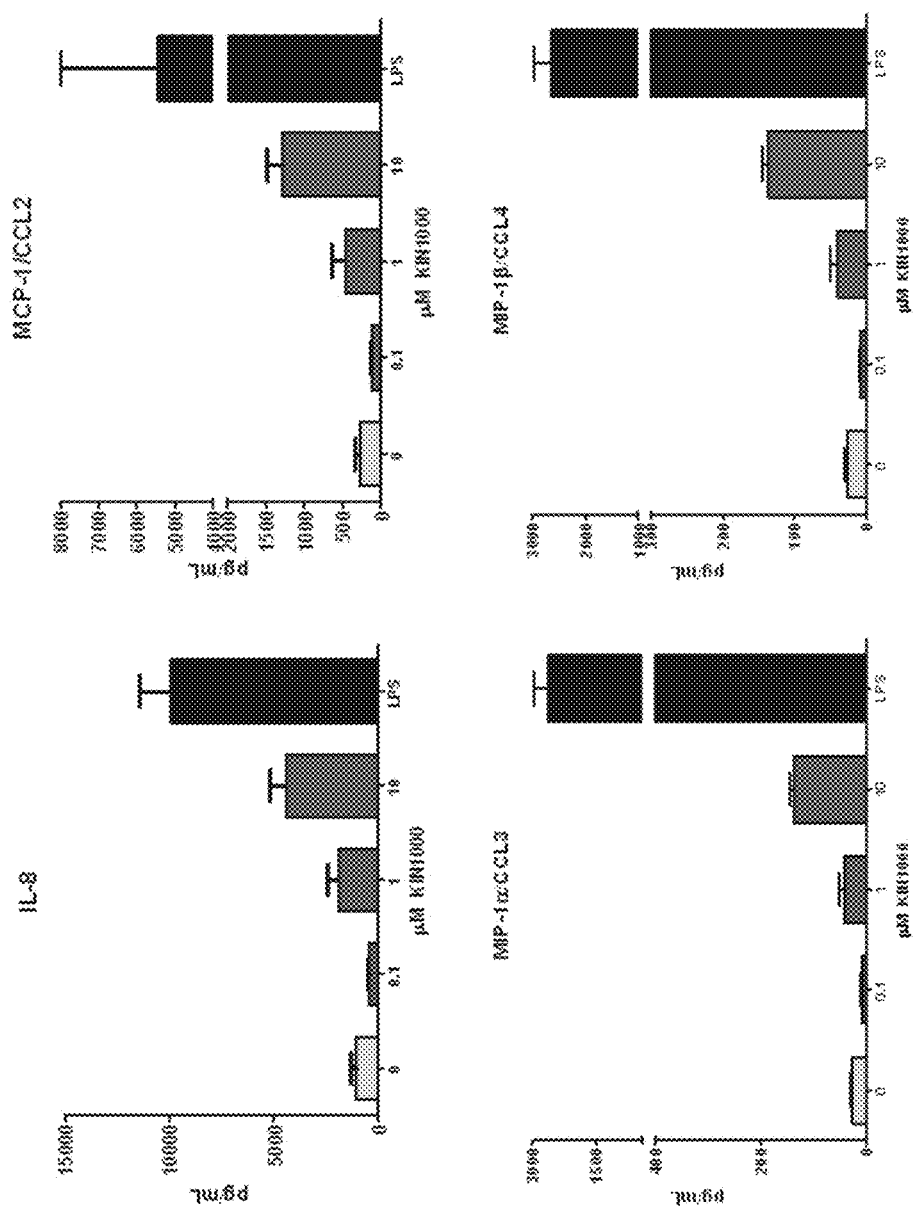
FIG. 4 shows Luminex® (Luminex Corp., Austin Tex.) quantified levels of cytokine expression induced by KIN1000. Human dendritic cells treated with increasing amounts of KIN1000 showed dose-dependent expression of cytokines including IL-8, MCP-1 (CCL2), and MIP-1α and β (CCL3 and CCL4, respectively).

KIN1000 was shown to induce expression of the chemokines IL-8, MCP-1, MIP-1α and MIP-1β by dendritic cells (FIG. 4).

Other cells from which cytokine secretion can be measured include, for example but without limitation, human peripheral blood mononuclear cells, human macrophages, mouse macrophages, mouse splenocytes, rat thymocytes, and rat splenocytes.

Example 4. Antiviral Activity and Pharmacological Properties Using Structure-Activity Relationship (SAR) Studies This Example describes optimization of compounds for antiviral action. First, a small analog derivative set is used to define a structural class. The active analogs that are identified in this first stage are then used to define a subset of structural classes of interest for further optimization (Stage 2).

Stage 2, derivative expansion. Stage 2 focuses on creating structural diversity and evaluating core variants. Structural derivatives are tested for biological activity in the IRF-3 translocation assay, antiviral activity, and cytotoxicity in one or more cell lines or peripheral blood mononuclear cells. Optimized molecules that show improved efficacy and low cytotoxicity are further characterized by additional measures of in vitro toxicology and absorption, distribution, metabolism, and elimination (ADME). Their mechanism of action and breadth of antiviral activity are also studied.

Chemical design in SAR studies. To design analog structures, the drug-like properties, metabolic lability, and toxic potential of the lead compounds are analyzed. Drug-like properties, as measured by Lipinski's Rules, and related physiochemical properties are primary indicators of bioavailability. Structural features that suggest metabolic and toxicological liabilities may indicate limited stability, reduced half-life, reactive intermediates, or idiosyncratic toxicity and will therefore be removed. A 5- to 10-compound analog set is constructed to remove or alter chemically reactive or metabolically susceptible structural features, thereby developing a preliminary SAR.

Compounds are tested for in vitro antiviral activity against HCV 2A, respiratory syncytial virus, dengue virus type 2, and influenza A virus strains. Viral protein and RNA levels are assessed following drug treatment using the assays described herein.

Following several iterative rounds of SAR, compounds are selected for characterization of their in vitro toxicological and ADME properties and for further mechanistic study. The SAR studies are designed to provide lead compounds with picomolar to nanomolar potency, which is adequate to support preclinical development.

In vitro pharmacology. In vitro pharmacology studies are performed to measure performance of the most promising analogs in one or more assays of intestinal permeability, metabolic stability and toxicity. Key in vitro characterization studies can include plasma protein binding; serum, plasma, and whole-blood stability in human and model organisms; intestinal permeability; intrinsic clearance; human Ether-à-go-go (hERG) channel inhibition; and genotoxicity.

For each analog, an HPLC- and/or HPLC-mass spectrometry-based analytical method is used to evaluate drug and metabolite concentrations in various test systems. Although the specific analytical method is optimized for each molecule, reverse-phase chromatography can be used alone or in combination with quadrupole mass spectrometry to characterize the identity and purity of several of the lead molecules. Initially, drug stability over time in increasing concentrations of serum, plasma, and whole blood from mammalian species (such as mouse, cynomolgus macaque, and human) is evaluated by HPLC, and a half-life is determined.

Prominent metabolites characterized by mass spectrometry. Human plasma protein binding are evaluated by partition analysis using equilibrium dialysis. For intestinal permeability modeling, apical-to-basolateral flux is assessed in the human epithelial cell line TC7. Hepatic clearance is estimated for a subset of the most promising analogs by measuring the rate of disappearance of the parent compound during incubation in human liver microsomes. As above, specific metabolites can be isolated and characterized.

In vitro toxicology. In vitro toxicology studies are performed to evaluate the potential cardiac and genetic toxicity of lead analogs. Automated patch-clamp is used to assess the impact of each compound on hERG channel currents in a recombinant Chinese hamster ovary (CHO) cell line transgenically expressing the human Kv11.1 gene. Concentrations up to the lesser of 30 times the maximum serum concentration or the limit of solubility of each compound are evaluated in order to determine an IC50 for the molecule on the hERG channel. A subset of compounds is evaluated over a range of concentrations for their ability to induce mutation reversion in *Salmonella typhimurium* strains TA98 and TA100 or to promote micronucleus formation in CHO cells in culture.

Example 5. Activation of Gene Expression by KIB1000 and Derivative Compounds

Gene expression in HeLa cells. Cultured human cells were treated with 20 µM, 10 µM, 5 µM of compound or a DMSO control and incubated for up to 24 hours. Cells were harvested and RNA was isolated using the QIAshredder columns and RNeasy Mini Kit (Qiagen) according to manufacturer instructions. Reverse transcription was performed and the cDNA template was used for quantitative real-time PCR. PCR reactions were performed using commercially available, validated TaqMan gene expression assays (Applied Biosystems/Life Technologies) according to manufacturer instructions. Gene expression levels were measured using a relative expression analysis ($\Delta\Delta Ct$).

Gene expression in PH5CH8 cells. Cultured human cells were treated with 10 uM, 5 uM, 1 uM or a DMSO control and incubated for up to 24 hours. Cells were harvested and RNA was isolated using the QIAshredder columns and RNeasy Mini Kit (Qiagen) according to manufacturer instructions. Reverse transcription was performed and the cDNA template was used for quantitative real-time PCR. PCR reactions were performed using commercially available, validated TaqMan gene expression assays (Applied Biosystems/Life Technologies) according to manufacturer instructions. Gene expression levels were measured using a relative expression analysis ($\Delta\Delta Ct$).

Gene expression in HUVEC primary cells. Cells were thawed and seeded in 6-well plates at $2.4 \times 10^4$ cells per well and allowed to grow to 80% confluence, typically 5 days in culture with fresh media replaced every 48 hours. Compound was added at 10 µM, 1 µM or a DMSO control and incubated for up to 24 hours. Cells were harvested and RNA was isolated using the QIAshredder columns and RNeasy Mini Kit (Qiagen) according to manufacturer instructions. Reverse transcription was performed and the cDNA template was used for quantitative real-time PCR. PCR reactions were performed using commercially available, validated TaqMan gene expression assays (Applied Biosystems/Life Technologies) according to manufacturer instructions. Gene expression levels were measured using a relative expression analysis ($\Delta\Delta Ct$).

Figure 5A:
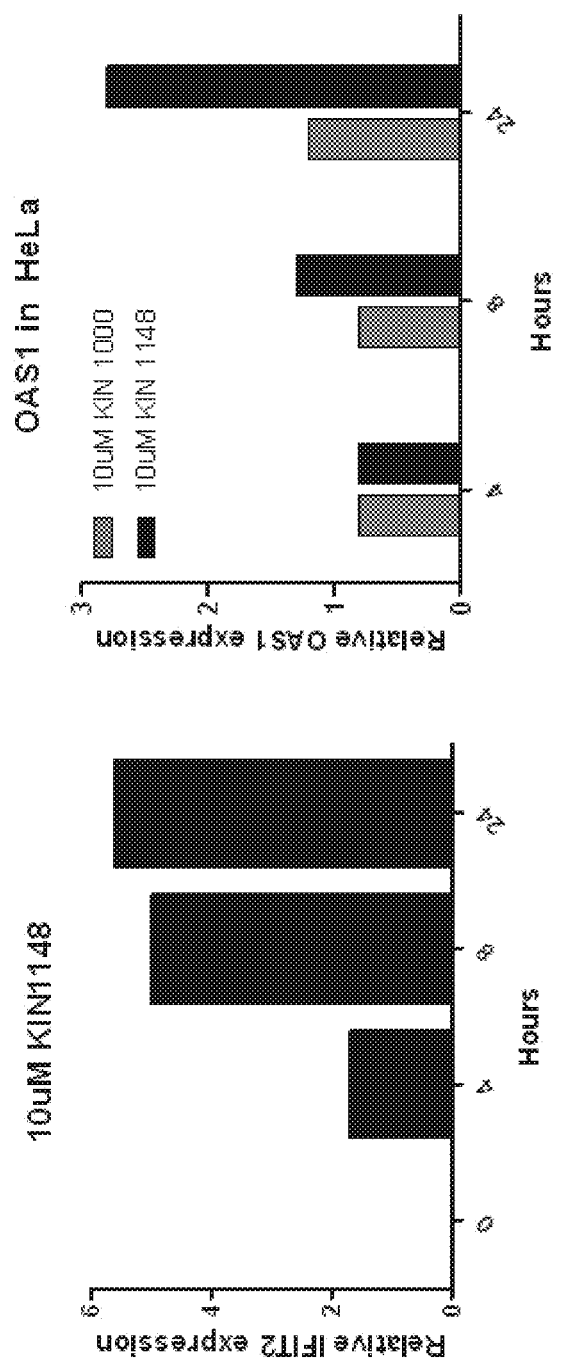
FIGS. 5A-5C show induction of gene expression by KIN1000 and its derivative compound KIN1148.
Figure 5B:
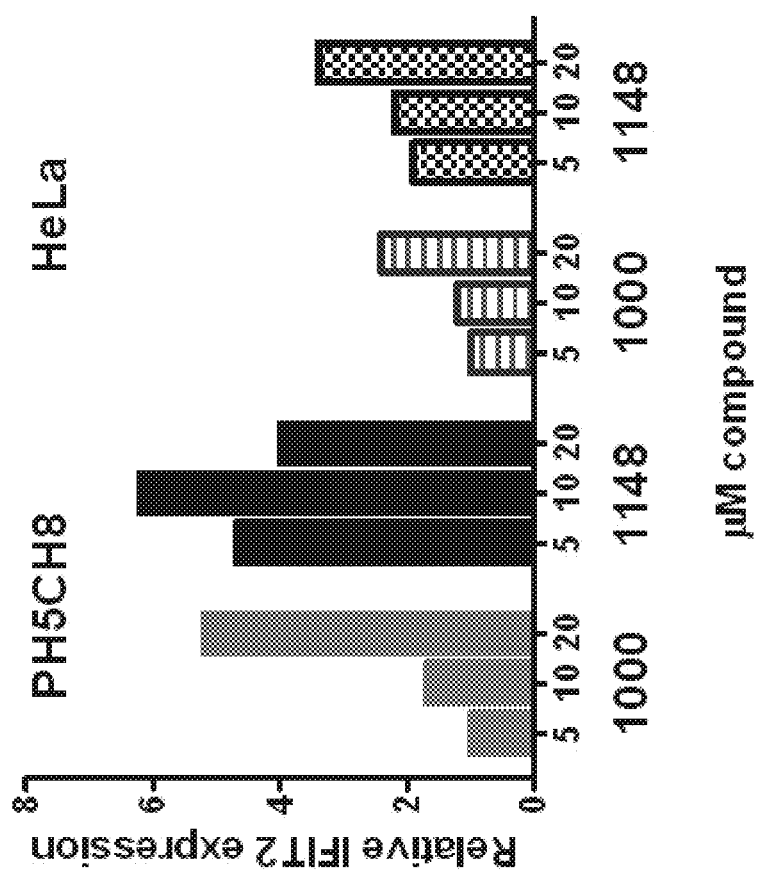
Figure 5C:
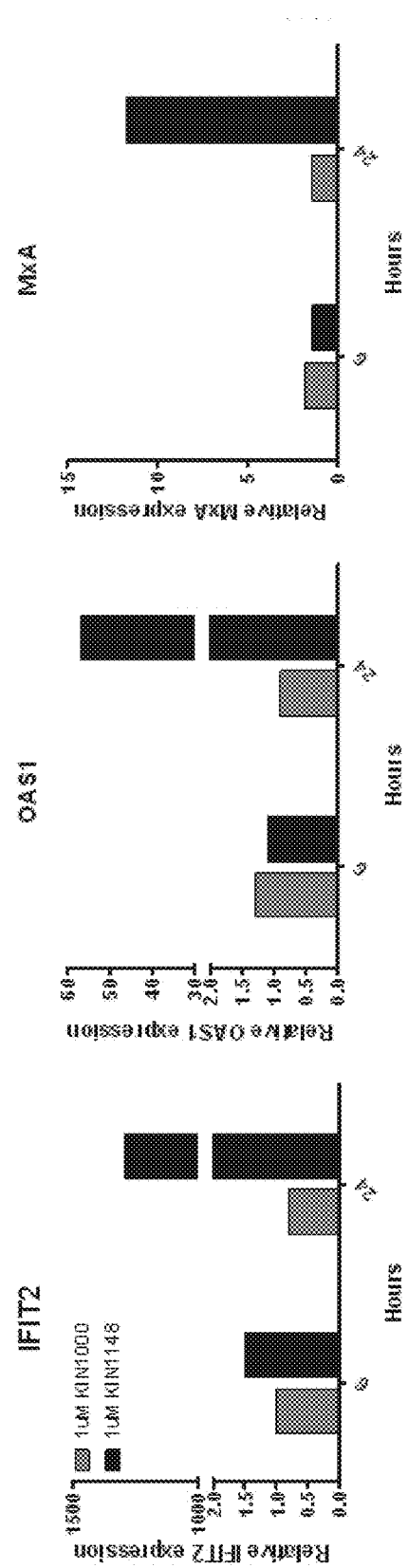

FIG. 5 shows induction of gene expression by KIN1000 and its derivative compound KIN1148. FIG. 5A shows gene expression levels of IFIT2 (left) and OAS1 (right) in HeLa cells over time from 4-24 hours post treatment with 10 µM KIN1000 (grey) or 10 µM KIN1148 (black). FIG. 5B shows gene expression levels of IFIT2 in PH5CH8 cells (left) treated with KIN1000 (solid grey bars) or KIN1148 (solid black bars), and in HeLa cells (right) treated with KIN1000 (grey striped bars) or KIN1148 (black checked bars). In each test group, the three vertical bars represent 5, 10, and 20 µM compound (KIN1000 or KIN1148), respectively. FIG. 5C shows gene expression levels of IFIT2 (left), OAS1 (center), and MxA (right) in primary HUVEC cells that were treated with 1 µM KIN1000 (grey) or 1 µM KIN1148 (black). The difference in axis scaling demonstrates that compounds are more active in a primary cell type. These data demonstrate that compounds are active in cells by inducing responsive gene expression.

Gene expression can be similarly assayed in cell types that include, without limitation: primary blood mononuclear cells, human macrophages, THP-1 cells, Huh 7 cells, A549 cells, MRCS cells, rat splenocytes, rat thymocytes, mouse macrophages, mouse splenocytes, and mouse thymocytes. Expression of other genes of interest can be assayed as described herein.

Example 6. Antiviral Activity of KIN1000 Against Various Viruses

Antiviral action in cell culture infection models. To further characterize the breadth of antiviral activity of optimized molecules, cell culture infection models are used to analyze different viruses, including but not limited to different strains of influenza virus, HCV, Dengue virus, RSV, and West Nile virus (WNV), an emerging public health concern. The studies include treating cells with compound 2-24 hours prior to infection or treating cells up to 8 hours after infection. Virus production and cellular ISG expression are assessed over a time course to analyze antiviral effects of representative compounds from lead structural classes. IFNβ treatment is used as a positive control.

Virus production is measured by focus-forming or plaque assay. In parallel experiments, viral RNA and cellular ISG expression are measured by qPCR and immunoblot analyses. These experiments are designed to validate compound signaling actions during virus infection, and assess compound actions to direct innate immune antiviral programs against various strains of viruses and in the setting of virus countermeasures. Detailed dose-response analyses of each compound are conducted in each virus infection system to determine the effective dose that suppresses virus production by 50% (IC50) and 90% (IC90) as compared with control cells for both the pre-treatment and post-treatment infection models.

TABLE 2

Virus systems and study design for antiviral analysis of lead compounds

| Virus | Virus Strain | Study Design |
|---|---|---|
| HCV | H77 (genotype 1a) | Assays |
|  | JFH1 (genotype 2a) | Plaque or focus forming |
| FLU | High pathogenicity in mice | assays (infectious virus) |
|  | A/PR/8/34 (H1N1 mouse-adapted virus) | qPCR (RNA levels) |
|  | A/WSN/33 (H1N1 mouse-adapted neurovirulent virus) | Immunoblot and ELISA (protein levels) |
|  | Low pathogenicity in mice | Study Design |
|  | A/Texas/36/91 (H1N1 circulating virus) | Compound treatment of cells pre- and post-infection |
|  | A/Udorn/72 (H3N2) | Determine $EC_{50}$ and $EC_{90}$ |
|  |  | Inhibition of viral life cycle |

TABLE 2-continued

Virus systems and study design
for antiviral analysis of lead compounds

| Virus | Virus Strain | Study Design |
|---|---|---|
| WNV | TX02 (lineage 1) | |
| | MAD78 (lineage 2) | |

Example 7. Activity of KIB1000 and Derivative Compounds Against Respiratory Syncytial Virus HeLa cells were seeded the previous day in 6-well plates at $4 \times 10^5$ cells per well. The next day, the media was replaced with RSV in media without FBS at an MOI of 0.1. Virus binding occurred at 37° C. for 2 hours. After 2 hours the cells were washed with warm complete media and replaced with media containing drug at varying concentrations of 10 µM, 5 µM, 1 µM or a DMSO control. Cells were placed in a 37° C. incubator for 48 hours.

For virus detection and titration, HeLa cells were seeded in 96-well plates at $8 \times 10^3$ cells per well 24 hrs prior to collecting virus supernatant. After the 48 hour incubation period, the virus supernatant from the infected plate was harvested and used to infect these cells at a 1/10 final dilution. Cells were placed in a 37° C. incubator for 24 hours.

24 hours after infection, cells were washed twice with PBS and fixed with methanol/acetone solution. After fixing the cells were washed twice with PBS and replaced with blocking buffer (10% horse serum, 1 g/mL BSA and 0.1% Triton-100X in PBS) for 1 hour. The blocking buffer is replaced with binding buffer containing a 1/2000 dilution of primary antibody for 2 hours at room temperature. The primary antibody was a mouse monoclonal antibody against RSV. The cells were washed twice with PBS and replaced with binding buffer containing 1/3000 dilution of the Alexa Fluor-488 goat anti-mouse secondary antibody and a Hoechst nuclear stain for 1 hour at room temperature. The cells were washed twice with PBS and PBS is added to all wells. The 96-well plate is sealed and fluorescence activity associated with virus infectivity was determined by immunofluorescent assay using the Array Scan instrument (Thermo-Fischer).

Figure 6A:
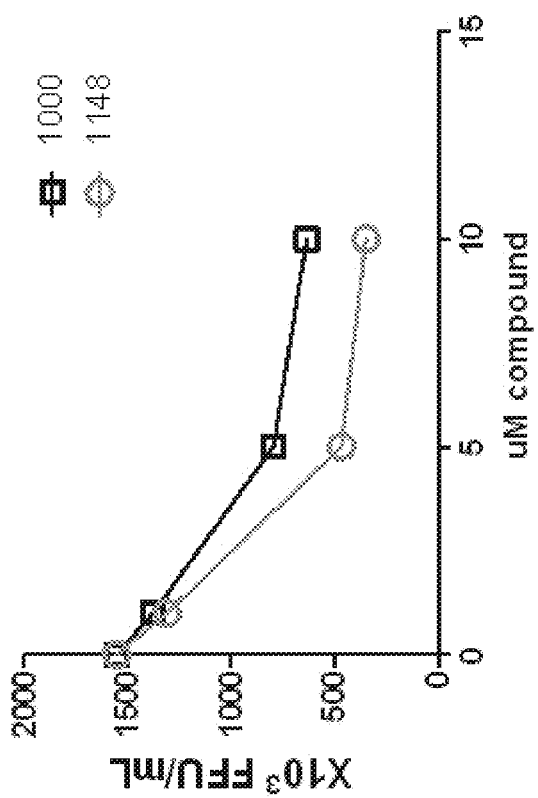
FIGS. 6A and 6B show antiviral activity of KIN1000 and KIN1148 against respiratory syncytial virus.
Figure 6B:
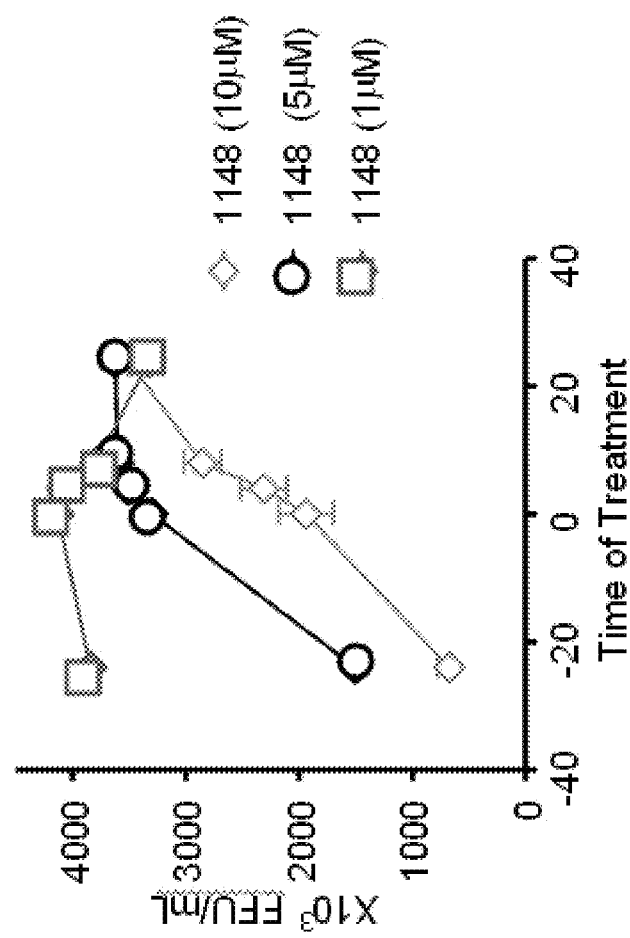

FIG. 6 shows experiments performed using the protocol of the Example, demonstrating the antiviral activity of KIN1000 and KIN1148 against respiratory syncytial virus. FIG. 6A shows that HeLa cells treated with increasing amount of KIN1000 and KIN1148 showed dose-dependent decrease in infection by RSV. FIG. 6B shows that KIN1148 showed antiviral activity against RSV when drug is added up to 24 hours prior to infection.

Treatment with compounds prior to infection. In variations of this method, the compounds are added at varying time points prior to infection with virus. Virus detection and titration is conducted as described.

Analog testing and SAR studies. Antiviral activity against RSV was used as a criterion to measure activity of structural derivatives of KIN1000. Table 3 shows select structural derivatives of KIN1000 that demonstrated antiviral activity against RSV. Compared to KIN1000 parent compound, these analogs showed varying levels of antiviral activity against RSV. +++=greater than 70% inhibition of infection, ++=greater than 50% inhibition, +=greater than 30% inhibition, −=less than 30% inhibition.

TABLE 3

| KIN | R3 | R1 | R2 | 10 um | 5 um | 1 um |
|---|---|---|---|---|---|---|
| 1000 | 3-bromophenyl | methyl | H | ++ | + | − |
| 1014 | 4-chlorophenoxymethyl | methyl | H | + | − | − |
| 1034 | 4-(N,N-dimethylsulfamoyl)phenyl | methyl | H | − | + | − |

TABLE 3-continued

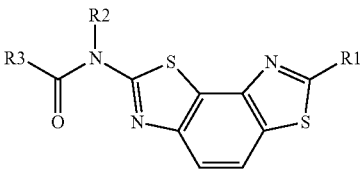

| KIN | R3 | R1 | R2 | 10 um | 5 um | 1 um |
|---|---|---|---|---|---|---|
| 1069 | 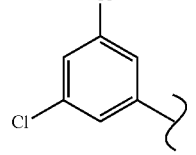 3,5-dichlorophenyl | H | H | ++ | + | − |
| 1072 | 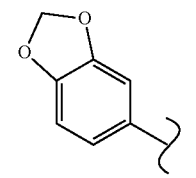 benzo[d][1,3]dioxol-5-yl | H | H | ++ | − | − |
| 1075 | 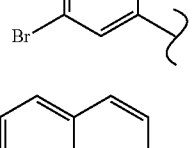 3-bromophenyl |  | 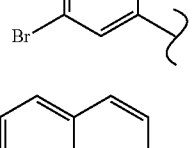 | + | − | − |
| 1148 | 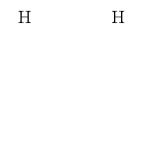 naphthalen-2-yl | H | H | +++ | ++ | − |
| 1169 | 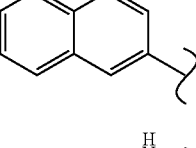 | 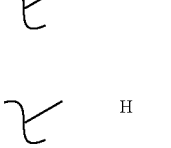 | H | +++ | ++ | − |
| 1170 | 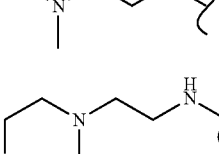 | 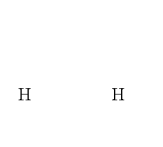 | H | ++ | − | − |
| 1203 | 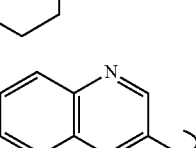 quinolin-3-yl | H | H | +++ | − | − |

Example 8. Activity of KINB1000 and Derivative Compounds Against Influenza A/Udorn/72 Virus Influenza A/Udorn/72 infection of H292 cells. 0.2×10⁶ H292 cells in RPMI1640+10% FCS were treated with 2 μM KIN1148 in a final concentration of 0.5% DMSO for 6 hours. Compound-containing media was aspirated and replaced with 1× MEM containing A/Udorn/72 at an MOI of 0.1 and placed at 37° C. in a CO² incubator. Two hours post infection, virus-containing media was aspirated and replaced with 1× MEM containing 1 ug/mL TPCK-treated Trypsin, 2 μM KIN1148, 0.5% DMSO. Cells were placed in 37° C. $CO_2$ incubator for 18 hours. After 20 hours post-infection, virus supernatants were collected and titred on MDCK cells.

Influenza A/Udorn/72 infection of HEK293 cells. 5×10⁵ HEK293 cells were infected with A/Udorn/72 at an MOI of 0.2 in 1×MEM. After 2 hours post-infection, virus-containing media was aspirated and replaced with 1×MEM containing 1 μg/mL TPCK-treated Trypsin, 10 μM KIN1148, 0.5% DMSO. Cells were returned to 37° C., $CO_2$ incubator for 18 hours. After 20 hours post-infection, virus supernatants were collected and titred on MDCK cells.

Titre in MDCK cells. 10 μL of infected supernatant was added to 2×10⁶ MDCK cells in the presence of 2 μg/mL TPCK-trypsin and placed in a 37° C. $CO_2$ incubator. After 8 hours, supernatant was removed and cells were fixed and stained with FITC-conjugated antibody specific for Influenza NP protein. Number of foci was quantitated using the ArrayScan instrument and software (Cellomics).

Figure 7:
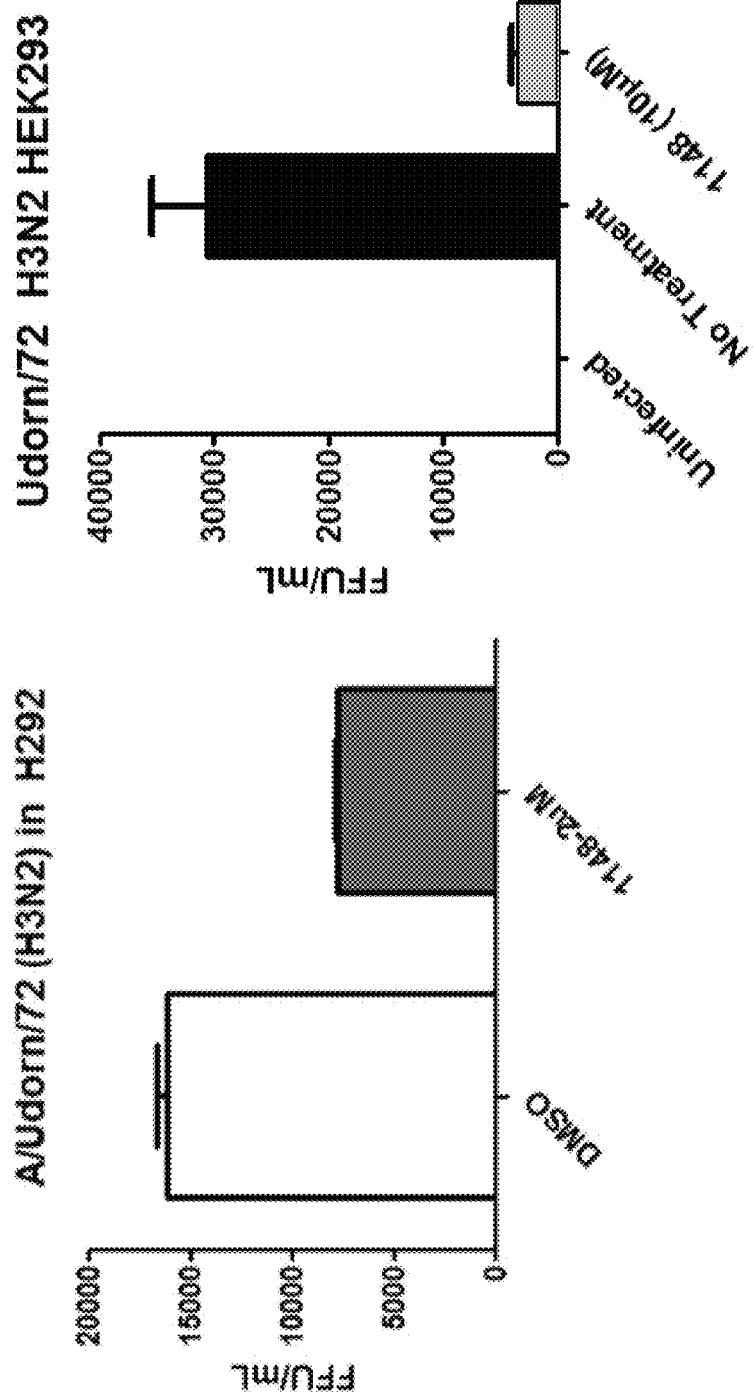
FIG. 7 shows antiviral activity of KIN1148 against Influenza A virus Udorn/72. H292 cells (left) and HEK293 cells (right) treated with 2 µM (H292) or 10 µM (HEK293) of KIN1148 showed decrease in infection by virus.

FIG. 7 shows antiviral activity of KIN1148 against Influenza A virus Udorn/72. H292 cells (left) and HEK293 cells (right) treated with 2 uM (H292) or 10 uM (HEK293) of KIN1148 showed decrease in infection by virus.

Example 9. Activity of KIN1000 and Derivative Compounds Against Dengue Virus Huh 7 cells were seeded the previous day in 6-well plates with $4 \times 10^5$ cells per well. The next day, the media was replaced with Dengue virus type 2 in media without FBS at an MOI of 0.25. Virus binding occurred at 4° C. for 1 hour. After 1 hour the cells were washed with warm complete media and replaced with media containing KIN1148 at varying concentrations of 10 uM, 5 uM, 1 uM or a DMSO control. Cells were placed in a 37° C. incubator for 48 hours.

Titre in Vero cells. Vero cells were seeded in 96-well plates at $8 \times 10^3$ cells per well 24 hrs prior to collecting virus supernatant. After 48 hrs, the virus supernatant was harvested and used to infect Vero cells at a 1/100 final dilution.

24 hrs after infection, Vero cells were washed 2× with PBS and fixed with methanol/acetone for 15 mins. After fixing the cells were wash 2× with PBS and replaced with blocking buffer for 30-45 mins. The blocking buffer was replaced with binding buffer containing a 1/2000 dilution of primary monoclonal antibody targeting the Envelope protein for 2 hrs. After 2 hrs, the cells were washed 2× with PBS and replaced with binding buffer containing 1/3000 dilution of the Alexa Fluor-488 goat anti-mouse secondary antibody and a Hoechst nuclear stain for 45 mins. After 45 mins cells were washed 2× with PBS and PBS was added to all the well. The 96-well plate was sealed and fluorescence activity associated with virus infectivity was determined by IF using the ArrayScan instrument and software (Cellomics).

Figure 8:
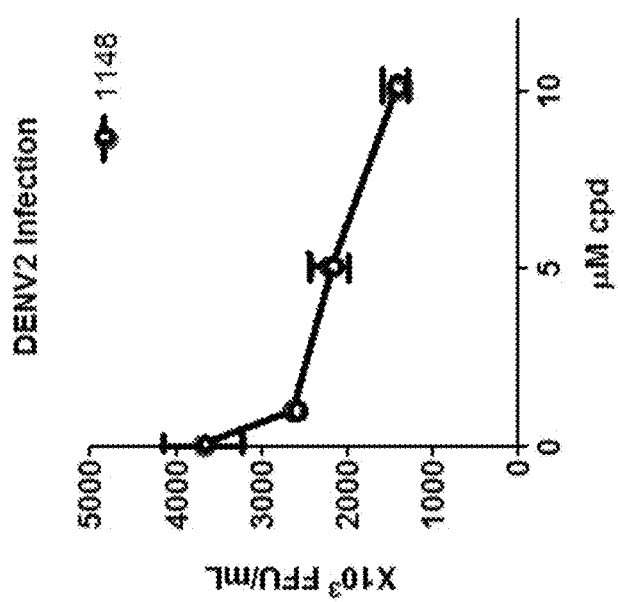
FIG. 8 shows antiviral activity of KIN1148 against Dengue virus type 2. Huh 7 cells treated with increasing amounts of KIN1148 showed dose-dependent decrease in infection by virus.

FIG. 8 shows the results of experiments performed using the protocol of this Example, demonstrating the antiviral activity of KIN1148 against Dengue virus type 2. Huh 7 cells treated with increasing amounts of KIN1148 showed dose-dependent decrease in infection by virus.

Example 10. Activity of KIN1000 and Derivative Compounds Against Hepatitis B Virus HepAD38 cells (Hep 2 cells expressing a regulated HBV genome) were grown for 72 hours in the presence of compound (concentrations 1-10 μM in 0.5% DMSO media). HepAD38 cells that do not express HBV were used as a negative control. Following 72 hours of treatment 100 μl of media was used in an ELISA to measure HBV surface antigen. The amount of HBV surface antigen produced by the cells was measured in the supernatants by ELISA commercially available HBV sAg ELISA from Creative Diagnostics, N.J.

Figure 9:
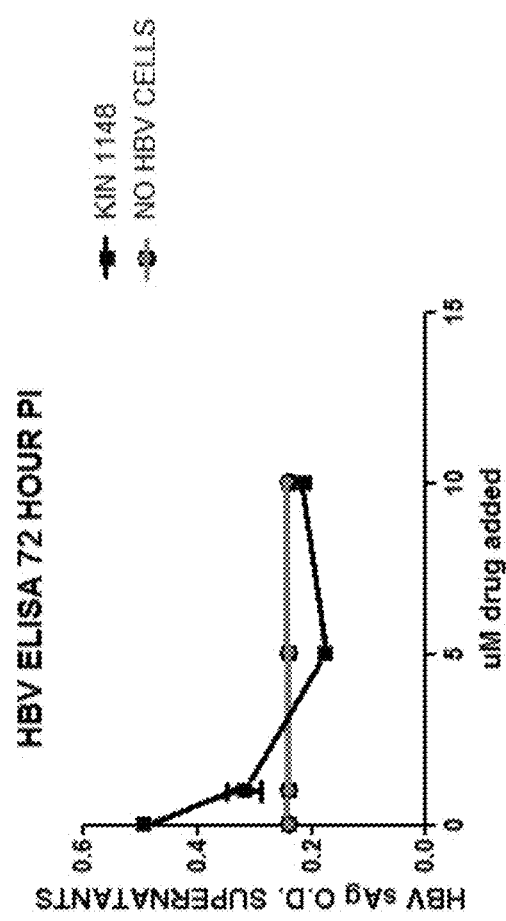
FIG. 9 shows antiviral activity of KIN1148 against Hepatitis B virus. HepAD38 cells treated with increasing amounts of KIN1148 showed dose-dependent decrease in supernatant levels of virus. The O.D. value that represents no HBV in the supernatant is shown by a horizontal line labeled "NO HBV CELLS."

FIG. 9 shows the results of experiments performed using the protocol of this Example, demonstrating the antiviral activity of KIN1148 against Hepatitis B virus. HepAD38 cells treated with increasing amounts of KIN1148 showed dose-dependent decrease in supernatant levels of virus.

Example 11. In Vivo Pharmacokinetic, Toxicological, and Antiviral Properties of Optimized Drug Leads in Relevant Preclinical Animal Models Preclinical pharmacokinetic and tolerability profiling. The in vivo pharmacokinetic (PK) profile and tolerability/toxicity of KIN1000 and related compounds are evaluated in order to conduct further characterization of their antiviral activity in animal models of influenza virus and WNV infection. Mouse is the chosen test species for these studies since it is the most commonly used rodent model of WNV and influenza.

A reverse-phase, HPLC-MS/MS detection method is used for measuring the concentration of each compound in mouse plasma. Prior to PK profiling, an initial oral and intravenous formulation for each compound is developed using a limited formulation component screen that is largely focused on maximizing aqueous solubility and stability over a small number of storage conditions. Any of the analytical methods as are known in the art can be used to measure formulation performance. A formulation is developed for each compound following a three tiered strategy:

Tier 1: pH (pH 3 to 9), buffer, and osmolality adjustment

Tier 2: addition of ethanol (<10%), propylene glycol (<40%), or polyethylene glycol (PEG) 300 or 400 (<60%) co-solvents to enhance solubility Tier 3: addition of N—N-dimethylacetamide (DMA, <30%), N-methyl-2-pyrrolidone (NMP, <20%), and/or dimethyl sulfoxide (DMSO, <20%) co-solvents or the cyclodextrins (<40%) as needed to further improve solubility.

For compounds that demonstrate adequate performance in in vitro antiviral, mechanistic, ADME, and toxicology studies, a preliminary mouse PK study is performed. See Table 3. Each compound is administered as a single dose to animals by oral gavage (<10 ml/kg) or i.v. bolus injection (<5 ml/kg) after an overnight fast. Multiple animals are dosed for each dosing group such that 3 animals can be sampled at each time point. Blood samples are collected by retro-orbital sinus prior to dosing and at 5, 15, and 30 minutes, and 1, 2, 4, 8, and 24 hours post-dosing. Drug concentrations are measured according to the previously developed bioanalytical method. Pharmacokinetic parameters are evaluated using the WinNonlin software.

TABLE 4

| Study | Experimental design | Route of administration | Outcomes |
| --- | --- | --- | --- |
| Mouse PK | Single dose pharmacokinetic study | IV and Oral | Oral bioavailability, $C_{max}$, $t_{1/2}$, CI, $V_d$, $AUC_{0-24, 0-\infty}$ |
| Mouse tolerability | Phase 1: ascending dose tolerability and MTD determination; Phase 2: placebo controlled 7-day toxicity at MTD | Oral | MTD, acute toxicity, hematology, serum chemistry, gross pathology |

Based upon performance in exploratory PK studies, compounds are further evaluated for preliminary tolerability and toxicity in mice prior to their characterization in antiviral models. Tolerability studies are performed in two stages: an initial dose escalation stage (up to 5 doses, each separated by a 5-day washout period) to determine the maximum tolerable dose (MTD, Phase 1), followed by seven daily administrations of the MTD to evaluate acute toxicity (Stage 2). See Table 3. All doses are administered by oral gavage. In an exemplary experiment, five animals of each sex are placed on-study in stage 1 and 15 animals per sex per dosing group in Stage 2. Study endpoints include a determination of the MTD, physical examination, clinical observations, hematology, serum chemistry and animal bodyweights. Gross pathology is performed on all animals whether found dead, euthanized in extremis, or at the intended conclusion of the experiment. The toxicology studies are primarily exploratory in nature and intended to identify early toxicological endpoints, and drive selection of lead candidates for antiviral animal models.

TABLE 5

In vivo studies of compound actions against WNV and influenza virus

| Experiment | Analysis | Goal | Exemplary No. of Mice* |
|---|---|---|---|
| Effective compound dose determination | Viral burden analysis in serum | Define in vivo $EC_{50}$ and $EC_{90}$ | 238 |
| Viral pathogenesis study 1: $EC_{50}$ and $EC_{90}$ Treatment | Time to moribund state, clinical scoring for pathologic signs of infection | Define compound action toward limiting viral pathogenesis | 739 |
| Viral pathogenesis study 2: $EC_{50}$ and $EC_{90}$ treatment and time course analysis | Viral burden analysis in serum and various target organs | Define compound action toward limiting virus replication and spread | 1056 |
| Viral pathogenesis study 3: (neuroinvasion model) $EC_{50}$ and $EC_{90}$ treatment | Time to moribund state, clinical scoring for pathologic signs of infection | Define compound action toward limiting viral pathogenesis in the CNS | 370 |

*Numbers reflect an average of at least two iterations of each experiment

Evaluation of antiviral properties and immune protection using mouse infection models. Optimized compounds are selected based on compound pharmacokinetic, antiviral, and innate immune actions for further evaluation in preclinical mouse models of infection. See Table 4. Innate immune actions of the compounds are measured, and their ability to protect mice from WNV and influenza virus challenge is assessed. For the WNV infection model, subcutaneous footpad infection of wild-type C57Bl/6 mice with the virulent lineage 1 strain of WNV (WNV-TX) are performed. Non-surgical tracheal instillation is performed for influenza virus strains A/PR/8/34, A/WSN/33, and A/Udorn/72.

The influenza virus strains used for certain experiments are of two different subtypes (H1N1 and H3N2) and exhibit varying pathogenic properties and clinical presentations in C57Bl/6 mice. Mice are monitored for morbidity and mortality over a range of challenge doses (such as, 10 to 1,000 pfu of virus) either alone or in combination with compound treatment beginning 12 hours before or 24 hours after infection and continuing daily subject to the determined plasma half-life of the drug. Compound dose-response analysis and infection time course studies are conducted to evaluate compound efficacy to: 1) limit serum viral load, 2) limit virus replication and spread in target organs, and 3) protect against viral pathogenesis.

For WNV, in addition to serum, viral burden is assessed in lymph nodes, spleen, and brain; for influenza virus, viral burden is assessed in heart, lung, kidney, liver, and brain. Incorporated in the design of these experiments is the determination of an effective dose for 50% and 90% suppression of serum viral load (ED50 and ED90) by each compound after a standard challenge of 100 pfu of WNV-TX or 1,000 pfu of influenza virus. Serum viral loads are determined by qPCR of viral RNA at 24-hour intervals following compound treatment. The compound actions are tested at the ED50 and ED90 toward limiting WNV pathogenesis in the cerebral nervous system using a WNV neuroinvasion model of infection.

Mice are monitored for morbidity and mortality after standard intracranial challenge of 1 pfu of WNV-MAD, either alone or in combination with compound treatment beginning 24 hours after infection.

Example 12. Antiviral Activity of KIN1000 and Derivative Compounds In Vivo

Evaluation of antiviral properties of KIN1000 and derivative compounds using mouse infection models. Up to 5 of the most promising compounds will be selected for further evaluation in preclinical mouse models of infection with Influenza and/or respiratory syncytial virus. Table 6 lists the nonclinical studies to measure antiviral efficacy of KIN1000 and derivative compounds.

TABLE 6

Nonclinical studies to measure drug concentration and antiviral efficacy in vivo

| Study | Experimental design | Route Admi. | No. Cpds. | No. Animals | Outcomes |
|---|---|---|---|---|---|
| Mouse dosing | Drug measured in blood at 3 dose levels; 2, 8, 24 hours post treatment | Oral/IP | ≤5 | 120 | Drug concentration in blood; HPLC reverse phase |
| Mouse Influenza Model | Tracheal instillation of A/WSN/33 or A/Udorn/72; drug treatment at 2 doses w/ placebo | Oral/IP | ≤5 | 480 | Mortality, viral titer in serum/target organs, body temp., bodyweight, clin. obs., cytokine levels |
| Mouse RSV Model | Tracheal instillation of RSV A2 Long strain; drug treatment at 2 doses w/ placebo control | Oral/IP | ≤5 | 240 | Mortality; bodyweight; target organ viral titer; innate immune gene expression; markers of inflammation |

Mouse influenza model. We will perform non-surgical tracheal instillation of influenza virus strains A/WSN/33 and A/Udorn/72. These influenza virus strains are two different subtypes (H1N1 and H3N2) and exhibit varying pathogenic properties and clinical presentations in C57Bl/6 mice. Lead derivatives of the KIN1000 family of compounds will be administered daily by oral gavage or IP administration over the entire course of infection (typically 2 weeks) at 2 dose levels plus a placebo control group. Five animals per sex and per group will be evaluated for endpoints, including but not limited to daily clinical observations, mortality, body weight, and body temperature. Three animals per sex will be used to measure virus titer in serum, heart, lung, kidney, liver, and brain. Cytokine expression at various time points during infection in compound-treated versus control animals will be assayed.

Mouse RSV model. We will perform non-surgical tracheal instillation of respiratory syncytial virus A2 long strain. BALB-c mice will be infected at a dose of RSV A2 virus that does not cause cytopathic effects followed by daily oral or IP administration of compound at 2 dose levels or a placebo control for up to 21 days. Mice will be monitored as described above, including inspection for morbidity and mortality, viral titer in serum and blood, cytokine secretion, increased immune cell populations, and innate immune gene expression.

Example 13. Adjuvant Activity of KIN1000 and Derivative Compounds In Vivo

To characterize the breadth of adjuvant activity of KIN1000 and related compounds, in vivo animal models of vaccination and vaccination plus protection are used. The studies include priming animals including but not limited to rats and mice with compound alone or in combination with an antigen and then assessing the adjuvant effect.

Adjuvant effect is measured by assays for modified, enhanced immune humoral and cellular responses. Humoral responses are assessed over time at discrete times post vaccination and/or boosting by collecting blood for sera and determining relative concentrations of antibody classes (IgM, IgG, IgA or IgE) and/or isotypes including IgG1, IgG2a, IgG2b, IgG2c, IgG3 for IgG antibodies. Moreover, affinity and avidity of the generated antibodies is also determined. In instances in which the vaccine preparation includes a combination of compound and antigen, the neutralizing activity of the generated antibodies is also determined.

Cellular mediated immune responses induced by the compounds are measured by established methods in the field including ex vivo stimulation of peripheral blood mononuclear cells, lymph nodes, splenocytes or other secondary lymphoid organs with the antigen and measurement of cytokine or chemokine production in the supernatant at several times thereafter. Cytokines measured include Th1 type of cytokines including but not limited to IFN gamma and TNF alpha, Th2 type cytokines including but not limited to IL-4, IL-10, IL-5 and IL-13 and Th17 cytokines including but not limited to IL-17, IL-21 and IL-23. Chemokines elicited by the compounds are also measured including but not limited to RANTES, IP-10, MIP1a, MIP1b, and IL-8. T cell antigen specific production of cytokines can also be measured by intracellular cytokine staining with fluorescently labeled specific antibodies and flow cytometry or by ELISPOT. Both CD4+ ad CD8+ T cell populations are studied.

Measurement of adjuvant activity at the cellular level is also determined by immunophenotyping of surface markers of activation by flow cytometry. CD8 T cell antigen-specific responses are also evaluated by intracellular cytokine staining of perforin, cell surface marker expression or proliferation assays including thymidine incorporation.

These experiments are designed to validate compound adjuvant activity in different combinations of prime-boost schemes and assess how the effects of KIN1000 or related compounds on the innate immune antiviral programs shape the adaptive immune responses mounted to the antigen in the vaccine preparations.

Detailed immune response analyses of each compound as described above are conducted with each selected antigen to determine the immune correlates for that particular antigen(s) and compound formulation. These results guide the protection studies in which animals vaccinated and boosted with combinations of select optimized compounds and desired antigen(s) formulations from select infectious agents are later challenged with doses of infectious agent that are known to result in disease or death of the animal. Protection afforded by vaccination is typically measured by monitoring of clinical symptoms and survival.

Figure 10:
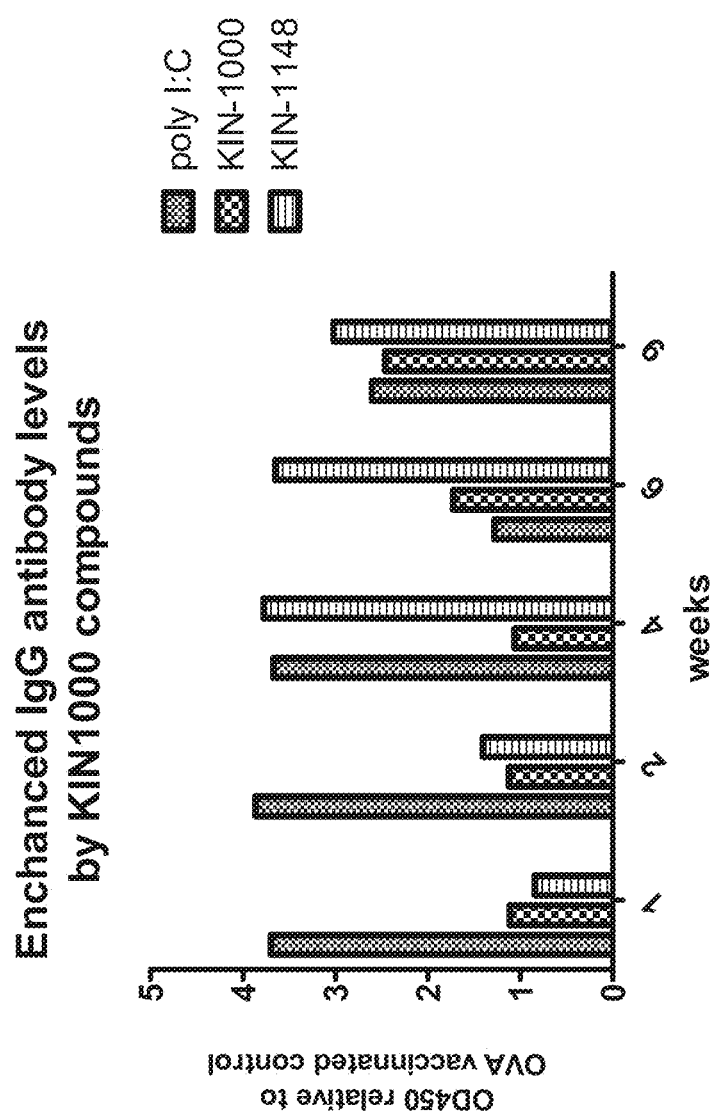
FIG. 10 shows IgG antibody production induced by KIN1000 and KIN1148 in vivo. Animals (Lewis female rats, 10-12 weeks old) were vaccinated with suspensions of OVA in PBS, OVA+polyI:C, OVA+KIN1000 or OVA+KIN1148 subcutaneously in the footpad and base of tail (0.025 mL injection volume per site). Animals were boosted identically at 2 and 8 weeks post priming. Animals were bled at the indicated time points, sera was prepared and antibody levels were detected by ELISA. OD450 values for vaccine preparations containing KIN1000 (large checked bars) and KIN1148 (horizontal striped bars) were normalized to values obtained from animals that received OVA in PBS alone as vaccines. Poly I:C (small checked bars) was used as a control adjuvant.

A proof of concept experiment was performed. LEWIS female rats at 10-12 weeks of age were primed with suspensions of antigen (ovalbumin, 0.2 mg/Kg) and KIN1000 (1 mg/Kg) or KIN1148 (1 mg/mL) in phosphate saline buffer (PBS) on day zero. Control animals received ovalbumin (OVA, InvivoGen Inc.) in PBS or OVA with poly I:C (0.1 mg/Kg, InvivoGen Inc.). Animals were boosted at weeks 2, and 8. Vaccines were delivered subcutaneously in the footpad and base of the tail for priming and on the footpad and flank for the boosts (0.025 mL/site). Blood samples were collected by tail bleed and processed to serum at 0, 1, 2, 4, 6, and 9 weeks post priming. Titers of OVA specific antibodies were determined by ELISA using anti IgM, anti IgG and anti IgG isotype specific antibodies. FIG. 10 shows IgG antibody levels relative to OVA alone vaccinated controls in OVA+KIN1000 and OVA+KIN1148 vaccinated animals.

Figure 11:
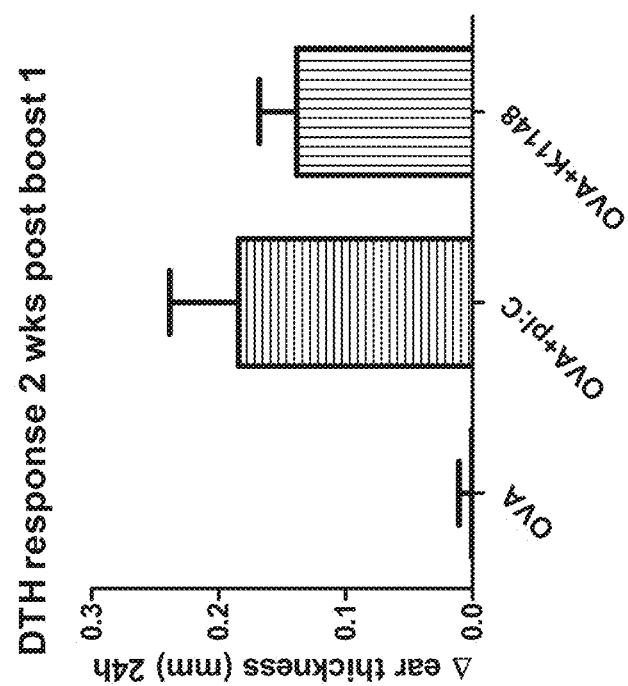
FIG. 11 shows cellular response elicited by KIN compound vaccination. Delatyed type hypersensitivity responses elicited 2 weeks after the first boost (4 weeks post prime) were measured. Animals were challenged by injection of 0.02 mL of PBS (left ear pinna) or 0.02 mL of OVA (1 mg/mL) in PBS (right ear pinna) at indicated time point. 24 hours later ear thickness was measured with calipers. The calculated difference between right ear and left ear is shown. "OVA+K1148" (vertical striped bar)=difference in ear thickness in animal injected with vaccine containing KIN1148. Poly I:C ("OVA+pI:C;" horizontal striped bar) was used as a control adjuvant.

Measurement of cell-mediated adjuvant activity is also determined by determining delayed type hypersensitivity (DTH) to an antigen. In the same proof of concept experiment, cellular responses were evaluated by determining the delayed type hypersensitivity reaction to challenge with OVA 2 weeks after the first boost. Animals were sedated with isoflurane and injected with PBS or OVA (0.02 mL of 1 m/gmL solution of OVA in PBS) in the pinna of the left and right ears, respectively. 24 hours later the difference in ear thickness was calculated. FIG. 11 shows measured difference between right ear and left ear thickness.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention claimed is:

1. A method of treating a viral infection in a vertebrate, comprising administering to a vertebrate an effective amount of a compound represented by the formula

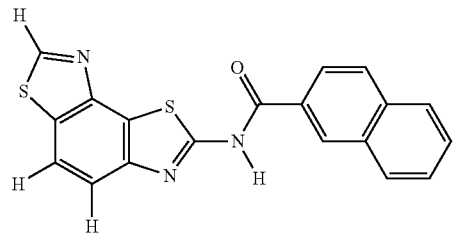 [SMILES: O=C(Nc1nc2ccc3scnc3c2s1)c1ccc2ccccc2c1]

or a pharmaceutically acceptable salt thereof, wherein said viral infection is caused by a virus selected from the group consisting of influenza virus, Dengue virus, Hepatitis B virus, and respiratory syncytial virus.

2. The method of claim 1, wherein the compound is administered as an adjuvant for a therapeutic vaccine.

3. The method of claim 2, wherein the method comprises vaccinating a vertebrate by additionally administering a vaccine against influenza virus, Hepatitis C virus, Dengue virus, or respiratory syncytial virus.

4. A method of modulating the innate immune response in a eukaryotic cell, comprising administering to a eukaryotic cell a compound represented by the formula

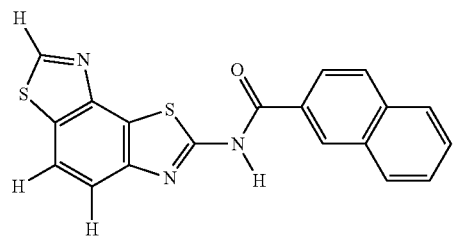 [SMILES: O=C(Nc1nc2ccc3scnc3c2s1)c1ccc2ccccc2c1]

or a pharmaceutically acceptable salt thereof, wherein said modulating is activation of interferon regulatory factor-3 (IRF-3).

5. A method of claim 4, wherein the cell is in vivo.

6. A method of claim 4, wherein the cell is in vitro.

* * * * *